US009297752B2

(12) United States Patent
Shimokawa et al.

(10) Patent No.: US 9,297,752 B2
(45) Date of Patent: Mar. 29, 2016

(54) OBJECT OBSERVING APPARATUS, OBJECT OBSERVING METHOD, AND STORAGE MEDIUM

(71) Applicant: ADVANCED TELECOMMUNICATIONS RESEARCH INSTITUTE INTERNATIONAL, Soraku-gun, Kyoto (JP)

(72) Inventors: Takeaki Shimokawa, Soraku-gun (JP); Takashi Kosaka, Soraku-gun (JP); Okito Yamashita, Soraku-gun (JP); Masaaki Sato, Soraku-gun (JP)

(73) Assignee: Advanced Telecommunications Research Institute International, Kyoto (JP)

( * ) Notice: Subject to any disclaimer, the term of this patent is extended or adjusted under 35 U.S.C. 154(b) by 0 days.

(21) Appl. No.: 14/388,358

(22) PCT Filed: Apr. 4, 2013

(86) PCT No.: PCT/JP2013/060282
§ 371 (c)(1),
(2) Date: Sep. 26, 2014

(87) PCT Pub. No.: WO2013/154012
PCT Pub. Date: Oct. 17, 2013

(65) Prior Publication Data
US 2015/0090869 A1    Apr. 2, 2015

(30) Foreign Application Priority Data

Apr. 10, 2012    (JP) ................................. 2012-088924

(51) Int. Cl.
*G01D 18/00* (2006.01)
*G01N 21/47* (2006.01)
(Continued)

(52) U.S. Cl.
CPC .......... *G01N 21/4785* (2013.01); *A61B 5/0073* (2013.01); *A61B 10/0041* (2013.01);
(Continued)

(58) Field of Classification Search
CPC ........................... A61B 5/1455; G06T 11/003
See application file for complete search history.

(56) References Cited

U.S. PATENT DOCUMENTS

| 6,507,022 B1 | 1/2003 | Salmond et al. |
| 2009/0244546 A1 | 10/2009 | Terakawa |
| 2011/0142316 A1 | 6/2011 | Wang et al. |
| 2011/0306857 A1 | 12/2011 | Razansky et al. |

FOREIGN PATENT DOCUMENTS

| CN | 1310798 A | 8/2001 |
| CN | 102137618 A | 7/2011 |

(Continued)

OTHER PUBLICATIONS

Munk et al., "Noninvasively measuring the hemodynamics effects of massage on skeletal muscle: A novel hybrid near-infrared diffuse optical instrument," 2012, Journal of Bodywork & Movement Therapies, vol. 16, pp. 22-28.*

(Continued)

*Primary Examiner* — Kiho Kim
(74) *Attorney, Agent, or Firm* — Birch, Stewart, Kolasch & Birch, LLP

(57) ABSTRACT

In order to solve a problem that a local optical characteristic-changed region inside an object cannot be accurately estimated, an object observing apparatus includes: a light intensity information acquiring unit that acquires light intensity information received by each light-receiving probe; a light intensity change information acquiring unit that acquires, for each probe set, light intensity change information, from reference light intensity information and light intensity information; an estimating unit that acquires three-dimensional optical characteristic-changed region information, using the light intensity change information; and an output unit that outputs the optical characteristic-changed region information; the estimating unit including a correcting part that performs correction according to sensitivity attenuation in accordance with a depth; and a sparseness applying part that introduces sparseness for improving a space resolution, thereby acquiring the optical characteristic-changed region information. Accordingly, it is possible to accurately estimate a local optical characteristic-changed region inside an object.

14 Claims, 19 Drawing Sheets

(51) Int. Cl.
*A61B 10/00* (2006.01)
*A61B 5/00* (2006.01)

(52) U.S. Cl.
CPC .............. *A61B5/0042* (2013.01); *A61B 5/0091* (2013.01); *G01N 2201/121* (2013.01); *G01N 2201/12753* (2013.01)

(56) References Cited

FOREIGN PATENT DOCUMENTS

| EP | 2067432 A2 | 6/2009 |
|---|---|---|
| JP | 2005-328916 A | 12/2005 |
| JP | 2008-178546 A | 8/2008 |
| WO | WO 2012/027849 A1 | 3/2012 |

OTHER PUBLICATIONS

Atsushi Maki, et al. "Spatial and temporal analysis of human motor activity using noninvasive NIR topography" Medical Physics 22, (1995) pp. 1997-2005.

Atsushi Miyamoto, et al. "Hierarchical Bayes method for NIRS-DOT inverse problem and its phase diagrams", IEICE Technical Report, 2010, pp. 51-56.

Benjamin W. Zeff, et al "Retinotopic mapping of adult human visual cortex with high-density diffuse optical tomography", PNAS, Jul. 17, 2007, vol. 104, No. 29. pp. 12169-12174.

Christina Habermehl, et al. "Somatosensory activation of two fingers can be discriminated with ultrahigh-density diffuse optical tomography" NeuroImage 59 (2012) pp. 3201-3211.

Daisuke Yamashita, et al. "Development of Multi Channel Time Resolved Spectroscopy System and Application to Optical Mammography System," Journal of Japanese College of Angiology Vo. 47 (2007) pp. 11-16.

Yoko Hoshi, et al "Detection of dynamic changes in cerebral oxygenation coupled to neuronal function during mental work in man", Neuroscience Letter 150 (1993) pp. 5-8.

Extended European Search Report, dated Jan. 6, 2016, in related application No. EP13775156.2.

Niu et al., "Development of a Compensation Algorithm for Accurate Depth Localization in Diffuse Optical Tomography," Optics Letters 35:3:429-431 (Feb. 1, 2010).

* cited by examiner

Probe attachment location

| Probe interval | 26mm | 18.4mm | 13mm |
|---|---|---|---|
| Light absorbing member position | Estimation limit depth [mm] | | |
| (a) Center | 15.0 | 20.0 | 22.5 |
| (b) Middle point | 17.5 | 20.0 | 22.5 |
| (c) Light-transmitting probe | 17.5 | 17.5 | 20.0 |
| (d) Light-receiving probe | 17.5 | 17.5 | 20.0 |

FIG.13

| Probe interval | 18.4mm | 13mm |
| --- | --- | --- |
| Horizontal distance [mm] | Estimation limit depth [mm] | |
| 15.0 | 17.5 | 17.5 |
| 12.5 | 15.0 | 17.5 |
| 10.0 | 15.0 | 17.5 |

FIG.15

| Probe interval | 18.4mm | 13mm |
|---|---|---|
| Horizontal distance [mm] | Estimation limit depth [mm] | |
| 15.0 | 15.0 & 20.0 | 15.0 & 20.0 |
| 12.5 | 12.5 & 17.5 | 12.5 & 17.5 |
| 10.0 | 7.5 & 12.5 | 7.5 & 12.5 |

FIG.17

OBJECT OBSERVING APPARATUS, OBJECT OBSERVING METHOD, AND STORAGE MEDIUM

TECHNICAL FIELD

The present invention relates to an object observing apparatus and the like for outputting three-dimensional information indicating a local optical characteristic-changed region inside an object.

BACKGROUND ART

Since measurement using near-infrared light is simple and safe, it is used for non-invasive measurement of the brain functions (see Non-Patent Document 1) and detection of breast cancer (see Non-Patent Document 2). Diffuse optical tomography (DOT) is an attempt to reconstruct an optical characteristic change or the structure inside a living body from observation data, by calculating a diffusion process of near-infrared light, which is extensively scattered inside a living body. Examples of such near-infrared measurement include continuous-light measurement, time-resolved measurement, and frequency-resolved measurement. Continuous-light measurement is characterized in that the amount of information that can be obtained is small, but the cost is low, the measurement is robust to noise because a large amount of light is irradiated, and the sampling frequency is high. On the other hand, time-resolved measurement and frequency-resolved measurement are characterized in that the amount of information that can be obtained is large, but the measurement is significantly affected by noise, and the cost is high.

In many cases, near-infrared light does not penetrate a living body because it is extensively scattered inside the living body. Thus, for example, in measurement of the brain functions, reflection-type measurement is performed in which light-transmitting probes are arranged on the head surface, and light reflected by diffusion is observed using light-receiving probes also arranged on the head surface. In the measurement of the brain functions, simultaneous measurement using a large number of probes is necessary in order to cover the activity region, and, thus, continuous-light measurement is usually used.

Conventionally, probes are arranged at intervals of approximately 3 cm, which is considered to be suitable for measurement of the brain functions, and the observation result is obtained as topographic data (see Non-Patent Document 3). Meanwhile, in recent measurement of the brain functions, there have been many attempts to increase the number of probes per unit area, thereby performing DOT at high density. Accordingly, it becomes possible to discriminate multiple cortical activity regions in the visual area and the somatosensory area (see Non-Patent Documents 4 and 5).

CITATION LIST

Non-Patent Document

[Non-Patent Document 1] Y. Hoshi and M. Tamura, "Detection of dynamic changes in cerebral oxygenation coupled to neuronal function during mental work in man," Neurosci. Lett. 150 (1993) 5-8.

[Non-Patent Document 2] Daisuke Yamashita, Motoki Oda, Hiroaki Suzuki, Takeshi Yamanaka, Toshihiko Suzuki, Yukio Ueda, Kazuyoshi Ohta, Mitsuharu Miwa, Yutaka Hasegawa, Hiroyuki Kyushima, and Yutaka Yamashita, "Development of Multi Channel Time Resolved Spectroscopy System and Application to Optical Mammography System," J Jpn Coil Angiol, 47 (2007) 11-16.

[Non-Patent Document 3] A. Maki, Y. Yamashita, Y. Ito, E. Watanabe, Y. Mayanagi, and H. Koizumi, "Spatial and temporal analysis of human motor activity using noninvasive NIR topography," Med. Phys. 22 (1995) 1997-2005.

[Non-Patent Document 4] B. W. Zeff, B. R. White, H. Dehghani, B. L. Schlaggar, and J. P. Culver, "Retinotopic mapping of adult human visual cortex with high-density diffuse optical tomography," Proc. Natl. Acad. Sci. U.S.A. 104 (2007) 12169-12174.

[Non-Patent Document 5] C. Habermehl, S. Holtze, J. Steinbrink, S. P. Koch, H. Obrig, J. Mehnert, and C. H. Schmitz, "Somatosensory activation of two fingers can be discriminated with ultrahigh-density diffuse optical tomography," NeuroImage 59 (2011) 3201-3211.

SUMMARY OF INVENTION

Technical Problem

However, the above-described reflection-type continuous-light measurement provides the smallest amount of information among DOT, and, thus, ill-posed problems frequently occurs in estimating an activity source, and the estimation is difficult. The reflection-type continuous-light DOT has two main problems, which will be described below.

Firstly, in the reflection-type continuous-light DOT, which is of the reflection-type, since probes can be arranged only on the surface, and the sensitivity is exponentially attenuated in accordance with the depth as light is diffused, it is difficult to specify the depth of an activity source.

Secondly, in the reflection-type continuous-light DOT, since light is diffused in an object, spatial blurring occurs, which makes it difficult to improve the space resolution.

That is to say, conventional object observing systems cannot accurately estimate, as three-dimensional information, a local optical characteristic-changed region inside an object such as the brain.

Solution to Problem

For the first problem, an object observing apparatus of the present invention performs correction according to sensitivity attenuation in accordance with the depth. Furthermore, for the second problem, sparse estimation is performed as a method for improving the space resolution. The object observing apparatus of the present invention combines these two countermeasures, thereby realizing accurate three-dimensional DOT including the depth direction.

More specifically, a first aspect of the present invention is directed to an object observing apparatus, including: a reference light intensity information storage unit in which reference light intensity information, which is information regarding a light intensity at each light-receiving probe, and is information used as a reference, is stored; a light intensity information acquiring unit that, using a near-infrared measurement apparatus having at least one probe set consisting of a pair of a light-transmitting probe for transmitting light to an object that is to be observed and a light-receiving probe for receiving light, acquires light intensity information, which is information regarding a light intensity of light received by each light-receiving probe, in a case where light with a certain light intensity is transmitted from each light-transmitting probe forming each probe set to the object; a light intensity change information acquiring unit that acquires, for each probe set, light intensity change information, which is information regarding a light intensity change, from the reference light intensity information in the reference light intensity information storage unit and the light intensity information acquired by the light intensity information acquiring unit; an estimating unit that acquires optical characteristic-changed region information, which is three-dimensional information regarding a position with a light absorbance change inside the object, using the light intensity change information for each probe set; and an output unit that outputs the optical characteristic-changed region information acquired by the estimating unit; wherein the estimating unit includes: a sensitivity information storage part in which sensitivity information, which is information indicating a relationship between an optical characteristic change and a light intensity change, can be stored; a correcting part that performs correction according to sensitivity attenuation in accordance with a depth, using the sensitivity information; and a sparseness applying part that introduces sparseness for improving a space resolution, thereby acquiring the optical characteristic-changed region information. Note that the estimating unit may simultaneously perform the correction according to the sensitivity attenuation and the application of the sparseness for improving the space resolution.

With this configuration, it is possible to accurately estimate, as three-dimensional information, a local optical characteristic-changed region inside an object.

Furthermore, a second aspect of the present invention is directed to the object observing apparatus according to the first aspect, wherein the estimating unit further includes an arithmetic expression storage part, in which a first arithmetic expression, which is an arithmetic expression used for acquiring the optical characteristic-changed region information, is an arithmetic expression for calculating a solution of an inverse problem, and is a cost function for performing correction according to the sensitivity information, can be stored, the correcting part substitutes the sensitivity information for the first arithmetic expression, thereby acquiring first optical characteristic-changed region information, the sparseness applying part acquires final optical characteristic-changed region information using the sparseness for improving the space resolution, using the first optical characteristic-changed region information, and the output unit outputs the optical characteristic-changed region information acquired by the sparseness applying part.

With this configuration, it is possible to accurately estimate, as three-dimensional information, a local optical characteristic-changed region inside an object.

Furthermore, a third aspect of the present invention is directed to the object observing apparatus according to the second aspect, wherein, in the arithmetic expression storage part, a second arithmetic expression for performing hierarchical Bayesian estimation on an initial value is also stored, and the sparseness applying part substitutes the first optical characteristic-changed region information as an initial value for the second arithmetic expression, and executes the second arithmetic expression to perform hierarchical Bayesian estimation, thereby acquiring final optical characteristic-changed region information.

With this configuration, it is possible to accurately estimate, as three-dimensional information, a local optical characteristic-changed region inside an object.

Furthermore, a fourth aspect of the present invention is directed to the object observing apparatus according to any one of the first to third aspects, for use in observation of a brain function of a living body, wherein the object that is to be observed is the brain of the living body, and the reference light intensity information is information regarding a light intensity at each light-receiving probe measured at rest.

With this configuration, it is possible to accurately and easily estimate the brain activity.

Furthermore, a fifth aspect of the present invention is directed to the object observing apparatus according to any one of the first to third aspects, for use in screening of breast cancer, wherein the object that is to be observed is a breast, and the reference light intensity information is information regarding a light intensity at each light-receiving probe from a breast with normal cells.

With this configuration, it is possible to accurately and easily detect breast cancer.

Furthermore, a sixth aspect of the present invention is directed to the object observing apparatus according to any one of the first to fifth aspects, wherein each interval between the light-transmitting and light-receiving probes is not greater than 20 mm.

With this configuration, it is possible to more accurately estimate, as three-dimensional information, a local optical characteristic-changed region inside an object.

Advantageous Effects of Invention

The object observing system according to the present invention can accurately estimate, as three-dimensional information, a local optical characteristic-changed region inside an object.

BRIEF DESCRIPTION OF DRAWINGS

FIG. 13 shows a table of a result of Experiment 2 in this embodiment.

FIG. 15 shows a table of a result of Experiment 3 in this embodiment.

FIG. 17 shows a table of a result of Experiment 4 in this embodiment.

DESCRIPTION OF EMBODIMENT

Figure 1:
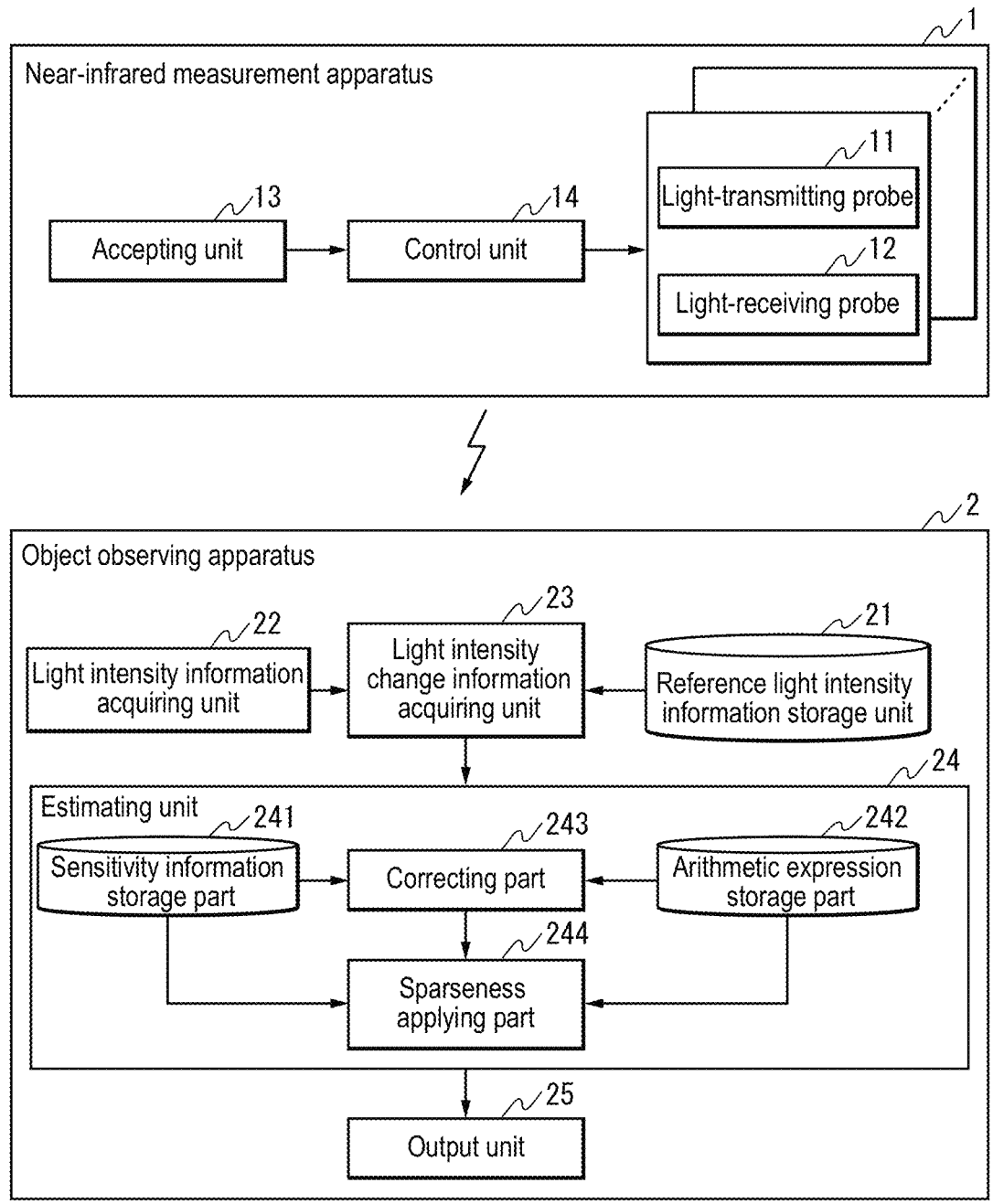
FIG. 1 is a block diagram of an object observing system in Embodiment 1.

Hereinafter, an embodiment of an object observing system and the like will be described with reference to the drawings. Note that constituent elements denoted by the same reference numerals perform the same operations in the embodiments, and, thus, a description thereof may not be repeated.

Embodiment 1

In this embodiment, an object observing system will be described that transmits near-infrared light to an object, receives light scattered inside the object, and outputs three-dimensional information indicating a local optical characteristic-changed region inside the object. In this case, the light typically received and used by an object observing apparatus forming the object observing system is not light that has penetrated an object, but backscattered light from the inside of an object.

FIG. 1 is a block diagram of an object observing system in this embodiment. The object observing system includes a near-infrared measurement apparatus 1 and an object observing apparatus 2.

The near-infrared measurement apparatus 1 includes light-transmitting probes 11, light-receiving probes 12, an accepting unit 13, and a control unit 14. The near-infrared measurement apparatus 1 has at least one probe set (also referred to as a channel) consisting of a pair of a light-transmitting probe 11 and a light-receiving probe 12. Note that the near-infrared measurement apparatus 1 typically has multiple probe sets.

The object observing apparatus 2 includes a reference light intensity information storage unit 21, a light intensity information acquiring unit 22, a light intensity change information acquiring unit 23, an estimating unit 24, and an output unit 25. Furthermore, the estimating unit 24 includes a sensitivity information storage part 241, an arithmetic expression storage part 242, a correcting part 243, and a sparseness applying part 244.

The light-transmitting probes 11 forming the near-infrared measurement apparatus 1 irradiate near-infrared light on an object (e.g., a head, a breast, or the like of a living body, in this example).

The light-receiving probes 12 typically receive light that has been absorbed or scattered inside an object and exits from the object. The probe arrangement density is more preferably 20 mm or less, extremely preferably 1.5 cm or less. The probe arrangement density refers to intervals between a light-transmitting probe 11 and a light-receiving probe 12. The higher the density at which the probes are arranged is, the better the configuration becomes. The reason for this is that, for example, the number of channels for detecting a state inside an object increases.

The light-transmitting probes 11 transmit light from one direction to an object that is to be observed. Furthermore, the light-receiving probes 12 typically receive light from the same direction as the one direction. Note that the same direction in this example is not limited to directions that exactly match each other, and there may be an angular difference therebetween (e.g., a large difference such as 30 degrees or 45 degrees). The same direction typically refers to a state in which a side from which the light-transmitting probes 11 transmit light and a side on which the light-receiving probes 12 receive light are on the same side of an object.

The accepting unit 13 accepts an instruction from the outside. This instruction is, for example, an irradiation instruction to irradiate near-infrared light on a living body.

If the accepting unit 13 accepts an irradiation instruction, the control unit 14 instructs the light-transmitting probes 11 to irradiate near-infrared light. Typically, if the light-transmitting probes 11 accept an irradiation instruction from the control unit 14, the light-transmitting probes 11 irradiate near-infrared light on an object.

In the reference light intensity information storage unit 21 forming the object observing apparatus 2, reference light intensity information is stored. The reference light intensity information is information regarding a light intensity at each light-receiving probe, and is information used as a reference. For example, in the case where the object observing apparatus 2 observes a brain activity, the reference light intensity information is information regarding a light intensity at each light-receiving probe 12 measured at rest. In the case of detecting breast cancer, the reference light intensity information is information regarding a light intensity at each light-receiving probe 12 from normal cells. There is no limitation on the procedure in which the reference light intensity information is stored in the reference light intensity information storage unit 21. The reference light intensity information and light intensity information, which will be described later, may be acquired in the same period.

The light intensity information acquiring unit 22 acquires light intensity information, using the near-infrared measurement apparatus 1 having at least one probe set consisting of a pair of a light-transmitting probe 11 for transmitting light to an object that is to be observed and a light-receiving probe 12 for receiving light. The light intensity information is information regarding a light intensity of light received by each light-receiving probe, in a case where light with a certain light intensity is transmitted from each light-transmitting probe 11 forming each probe set to the object. Note that the object that is to be observed is, for example, a brain, a breast, or the like of a living body.

The light intensity change information acquiring unit 23 acquires, for each probe set, light intensity change information, which is information regarding a light intensity change, from the reference light intensity information in the reference light intensity information storage unit 21 and the light intensity information acquired by the light intensity information acquiring unit 22.

The estimating unit 24 acquires optical characteristic-changed region information, using the light intensity change information for each probe set. The light intensity change information is the information acquired by the light intensity change information acquiring unit 23. Furthermore, the optical characteristic-changed region information is three-dimensional information regarding a position with a light absorbance change inside an object. Furthermore, the optical characteristic-changed region information also may be referred to as information regarding the amount of light absorbance change inside an object.

In the sensitivity information storage part 241 forming the estimating unit 24, sensitivity information can be stored. The sensitivity information is information indicating a relationship between an optical characteristic change (e.g., corresponding to X (described later)) and a light intensity change (e.g., corresponding to Y (described later)). The sensitivity information is, for example, a sensitivity matrix, which will be described later.

In the arithmetic expression storage part 242, arithmetic expressions used by the object observing apparatus 2 can be stored. In the arithmetic expression storage part 242, for example, a first arithmetic expression or a second arithmetic expression can be stored. The first arithmetic expression is, for example, an arithmetic expression used for acquiring the optical characteristic-changed region information, is an arithmetic expression for calculating a solution of an inverse problem, and is a cost function for performing correction according to the sensitivity information. Furthermore, the second arithmetic expression is, for example, an arithmetic expression for performing hierarchical Bayesian estimation on an initial value. The second arithmetic expression may be, for example, an L1 norm arithmetic expression.

The correcting part 243 performs correction according to sensitivity attenuation in accordance with the depth, using the sensitivity information in the sensitivity information storage part 241. More specifically, the correcting part 243 substitutes the sensitivity information for the first arithmetic expression, thereby acquiring first optical characteristic-changed region information. There is no limitation on the arithmetic expression for performing correction according to sensitivity attenuation in accordance with the depth.

The sparseness applying part 244 introduces sparseness for improving the space resolution, thereby acquiring optical characteristic-changed region information. Specifically, the sparseness applying part 244 acquires final optical characteristic-changed region information using the sparseness for improving the space resolution, using the first optical characteristic-changed region information as input. More specifically, the sparseness applying part 244 substitutes the first optical characteristic-changed region information as an initial value for the second arithmetic expression, and executes the second arithmetic expression to perform hierarchical Bayesian estimation, thereby acquiring final optical characteristic-changed region information. Note that the sparseness is preferably introduced through hierarchical Bayesian estimation, but an L1 norm also may be used. There is no limitation on the algorithm for introducing the sparseness. Furthermore, in the algorithm, the correcting part 243 and the sparseness applying part 244 may simultaneously operate.

More specifically, the estimating unit 24 operates as follows. That is to say, the estimating unit 24 reconstructs a three-dimensional light absorbance change map, from light intensity change information, which is a value indicating a change between the two amounts of light consisting of reference light intensity information, which is information regarding the amount of light measured on the base line, and information (light intensity information) regarding the amount of light measured when there is a light absorbance change.

In order to perform the reconstruction, the estimating unit 24 executes two steps consisting of a direct problem solving step and an inverse problem solving step. Firstly, in the direct problem solving step, the estimating unit 24 acquires a relationship between a light absorbance change and an observed light intensity change. Next, in the inverse problem solving step, the estimating unit 24 estimates the light absorbance change, from the relationship obtained in the direct problem solving step and the observed light intensity change. Note that a problem, in a case of estimating and acquiring values (e.g., X), using observed values (e.g., Y) in a number smaller than the number of values (e.g., X) that are to be estimated, is referred to as an ill-posed problem among inverse problems, and some sort of efforts such as regularization are necessary for solving the problem.

The object observing apparatus 2 uses the Rytov approximation in the direct problem solving step. The Rytov approximation is a known art, and, thus, a detailed description thereof has been omitted. According to the Rytov approximation, assuming that the amount of light $\Phi_0(r_s, r_d)$ transmitted from a source (the light-transmitting probe 11) at a position $r_s$ and reaching a detector (the light-receiving probe 12) at a position $r_d$, on the base line, becomes $\Phi(r_s, r_d)$ due to a light absorbance change inside an object by $\delta\mu_a$, the amount of light change generated $\Phi_{pert}(r_s, r_d)=\ln(\Phi_0(r_s, r_d)/\Phi(r_s, r_d))$ is represented by Equation 1 below. That is to say, Equation 1 represents the Rytov approximation.

$$\Phi_{pert}(r_s, r_d) = \int dr \frac{\Phi_0(r_s, r)\Phi_0(r, r_d)}{\Phi_0(r_s, r_d)} \delta\mu_a(r). \quad (1)$$

In this embodiment, the object observing apparatus 2 discretizes a region into voxels of "2.5 mm×2.5 mm×2.5 mm". Assuming that a voxel index is i, a channel index is j, and "$Y_j=\Phi_{pert}(r_{s(j)}, r_{d(j)})$, $X_i=\delta\mu_a(r_i)$, $A_{j,i}=\Phi_0(r_{s(j)}, r_i)\Phi_0(r_i, r_{d(j)})/\Phi_0(r_{s(j)}, r_{d(j)})$", the Rytov approximation expression in Equation 1 is represented by a linear equation "Y=AX". Note that "$Y=(Y_1, \ldots, Y_M)^T$" is an observed light intensity change in all channels, "$X=(X_1, \ldots, X_N)^T$" is a light absorbance change in all voxels, and A is a sensitivity matrix (exemplary sensitivity information) having $A_{j,i}$ as an element. The sensitivity matrix is stored in the sensitivity information storage part 241. Furthermore, the Rytov approximation expression or "Y=AX" may be stored in the arithmetic expression storage part 242. Hereinafter, it is assumed that the number of voxels is N and the number of channels is M as appropriate.

The value of $\Phi_0$ can be obtained using photon Monte Carlo simulation (see "Q. Fang and D. A. Boas, "Monte Carlo simulation of photon migration in 3D turbid media accelerated by graphics processing units," Opt. Express 17 (2009) 20178-20190."). Furthermore, depending on the shape of a medium, an approximate value of $\Phi_0$ can be preferably obtained using analytic solution with diffusion approximation (see "R. C. Haskell, L. O. Svaasand, T. T. Tsay, T. C. Feng, M. S. McAdams, and B. J. Tromberg, "Boundary conditions for the diffusion equation in radiative transfer," J. Opt. Soc. Am. A 11 (1994) 2727-2741.).

Next, the estimating unit 24 solves the inverse problem as follows. That is to say, the correcting part 243 forming the estimating unit 24 obtains an estimated solution using a Tikhonov regularization method in a case where a regularization term is normalized with a sensitivity term. Next, the sparseness applying part 244 performs hierarchical Bayesian estimation in which the value obtained by the correcting part 243 is used as an initial value.

Firstly, an operation of the correcting part 243 will be described in detail. In the arithmetic expression storage part 242, a cost function shown in Equation 2 below is stored. The correcting part 243 obtains a solution "$\hat{X}_R=\mathrm{argmin}_X C_R(X; \lambda)$", which minimizes the cost function. Note that "^" of "$\hat{X}$" is positioned directly above X.

$$C_R(X;\lambda) = \left\| \sum_y^{-\frac{1}{2}} (Y - AX) \right\|^2 + \lambda \left\| D^{\frac{1}{2}} X \right\|^2. \quad (2)$$

In Equation 2, the first term is an observation error term, and the second term is an L2 regularization term for preventing overfitting. The overfitting refers to excessive optimization of parameters to observation data. Furthermore, in Equation 2, $\lambda$ is a parameter for determining a regularization level. An optimum $\lambda$ value is determined by ABIC minimization, which is one of the information criteria, and is stored in the arithmetic expression storage part 242 (see "H. Akaike, "Likelihood and the Bayes procedure," In Bayesian Statistics (eds J. M. Bernardo et al., Univ. Press, Valencia) 143-166 (1980)."). Furthermore, $\Sigma_y$ is an observation noise covariance matrix of an observed value Y.

In Equation 2, D is a normalization term according to the sensitivity. The value of a sensitivity matrix A is exponentially attenuated in accordance with the depth. Thus, spatially uniform regularization may cause a bias in the estimation result. In order to prevent this problem, the normalization term causes the level of the regularization term at each location to match the level of the sensitivity. Note that D in Equation 2 is represented by Equation 3 below.

$$D=\text{diag}(A^T\Sigma_y^{-1}A+\beta I). \quad (3)$$

In Equation 3, diag represents a matrix constituted by diagonal components, and T in the upper right corner represents transposition of a matrix. Furthermore, I is an identity matrix, and $\beta$ is a sensitivity threshold for performing normalization. In this embodiment, it is assumed that the value of $\beta$ in all of the following analyses is, for example, a maximum value of the sensitivity at a voxel located at a depth of 22.5 mm or more from a probe surface, that is, "$\beta=\max_{z>22.5\ mm}[\text{diag}(A^T\Sigma_y^{-1}A)]$". Furthermore, if the regularization term is in the form of an L2 norm, an estimated solution $\hat{X}_R$ (where ^ is positioned directly above X) can be analytically obtained as shown in Equation 4. That is to say, Equation 4 is stored in the arithmetic expression storage part 242. The correcting part 243 obtains an estimated solution $\hat{X}_R$ using Equation 4.

$$\hat{X}_R=(A^T\Sigma_y^{-1}A+\lambda D)^{-1}A^T\rho_y^{-1}Y. \quad (4)$$

Next, an operation of the sparseness applying part 244 will be described in detail. Note that an estimated solution $\hat{X}_R$ using a Tikhonov regularization method in a case where a regularization term is normalized with a sensitivity term has some problems. That is, there are problems in which correction according to the sensitivity significantly acts on a portion not requiring the correction because a solution cannot be localized, resulting in a significant error in the estimated position, and in which the space resolution is low. Thus, in order to further improve the solution, the sparseness applying part 244 performs hierarchical Bayesian estimation in which the estimated solution $\hat{X}_R$ is used as an initial value. That is to say, the sparseness applying part 244 introduces "sparseness" where the estimated solution is represented in the minimum region. It narrows down results obtained by the operation of the correcting part 243 correcting the sensitivity to an important location, thereby realizing a high space resolution. With this operation, the depth is also more correctly estimated.

The hierarchical Bayesian estimation represents not only the generation of observation values but also the regularization as a hierarchical probability model as follows. Firstly, an observation model of an observed light intensity change Y at an internal light absorbance change X is represented by Equation 5 below.

$$P(Y|X)=N(Y|AX,\Sigma_y), \quad (5)$$

In Equation 5, a normal distribution of an average p and a covariance matrix $\Sigma$ is $N(x|\mu,\Sigma)$. $\Sigma_y$ is an observation noise covariance matrix of an observed value Y. Secondly, it is assumed that a solution X is given by normal distribution with a zero mean vector and a diagonal covariance matrix $\Lambda=\text{diag}(\lambda_1, \lambda_2, \ldots, \lambda_N)$ whose diagonal elements are adjustable parameters.

$$P(X|\Lambda)=N(X|0,\Lambda^{-1}). \quad (6)$$

This sort of prior distribution is referred to as automatic relevance determination (ARD) prior distribution. Furthermore, $\Lambda$ is obtained from a probability distribution shown in Equation 7 below.

$$P(\Lambda) = \prod_{i=1}^{N} \Gamma(\lambda_i | \lambda_{Pi}, \gamma_{Pi}), \quad (7)$$

In Equation 7, a gamma distribution with the average μ and the shape parameter γ is $\Gamma(x|\mu,\gamma)$. Furthermore, $\lambda_{pi}$ is an average of the prior distribution, and $\gamma_{pi}$ is a reliability parameter thereof. For example, it is assumed that "$\gamma_{pi}=0$". If "$\gamma_{pi}=0$", Equation 7 is non-informative prior distribution, and $\lambda_{pi}$ does not affect the probability model.

According to the Bayesian method, a posterior distribution $P(X,\Lambda|Y)$ of X and $\Lambda$ in a state where an observed value Y is given is obtained (see Equation 8).

$$P(X, \Lambda | Y) = \frac{P(X | \Lambda)P(\Lambda)}{P(Y)}. \quad (8)$$

However, a posterior distribution cannot be analytically obtained. Calculation of the posterior distribution can be considered as maximization of free energy using a variational Bayesian method as described later. The free energy is represented by Equation 9 below. In Equation 9, $f(\Lambda)$ is a prior distribution term. The free energy can be maximized by iterative calculation as described later.

$$F = -\frac{1}{2}\left[\left\|\sum_y^{-\frac{1}{2}}(Y-AX)\right\|^2 + \left\|\Lambda^{\frac{1}{2}}X\right\|^2 + f(\Lambda)\right]. \quad (9)$$

According to Equation 2 of the Tikhonov regularization method, a regularization parameter $\lambda$ common to all internal states $X_i$ is used and a uniform penalty is applied, so that a smoothed solution is obtained. On the other hand, according to Equation 9 of the hierarchical Bayesian estimation, a regularization parameter $\Lambda=\text{diag}(\lambda_1, \ldots, \lambda_N)$ that varies for each voxel is used and is applied to data, so that a sparseness effect can be obtained (see "A. C. Faul and M. E. Tipping, "Analysis of sparse Bayesian learning," Adv. Neural Inf. Process. Syst. 14 (2002) 383-389."). The sparseness applying part 244 substitutes the estimated solution $\hat{X}_R$ obtained using the Tikhonov regularization method for an initial value $\lambda_{0i}$ of iterative calculation (described later), and performs estimation. Exactly speaking, the sparseness applying part 244 performs scale correction of a noise term in Equation 5 and introduction of a smoothing filter in Equation 6, which will be described later.

Above, the outline of the hierarchical Bayesian estimation method has been described. Hereinafter, detailed settings will be described. Firstly, T time sample data sets are obtained in the measurement. Thus, extension is performed such that "$Y=(Y(1), \ldots, Y(t), \ldots, Y(T))$", and the light absorbance change is accordingly extended such that "$X=(X(1), \ldots, X(t), \ldots, X(T))$" in accordance with the time. Furthermore, the observation noise covariance matrix is set to a constant multiple of the noise covariance matrix measured on the base line "$\Sigma_y=\sigma^{-1}\Sigma_{y0}$", a prior distribution is given to its coefficient σ, and its value is determined by estimation (see Equation 10).

$$P(Y|X,\sigma)=N(Y|AX,\sigma^{-1}\Sigma_{y0}), P(\sigma)\propto\sigma^{-1}, \quad (10)$$

Furthermore, if the non-linear effect is high, for example, if the probe interval is 13 mm, this aspect is incorporated as noise, and a term proportional to a square value $Y^2$ of the observed value is added to the diagonal terms of the observation noise $\Sigma_y$. Furthermore, in order to prevent the solution from being too sparse, the solution X is obtained as "X=WZ" by multiplying a smoothing filter W by a sparse representation Z of the solution, and an ARD prior distribution is applied to Z. Accordingly, the probability distribution X is given as follows.

$$P(X|\Lambda) = N(X|0, W\Lambda^{-1}W^T). \quad (11)$$

Equation 11 is obtained by extending Equation 6 in a more suitable form. Note that, for example, W is a Gaussian filter having a full width at half maximum of 5 mm. In this case, the posterior distribution is given as Equations 12 and 13 below.

$$P(X, \Lambda, \sigma | Y) = \frac{P(Y, X, \Lambda, \sigma)}{P(Y)}, \quad (12)$$

$$\log P(Y, X, \Lambda, \sigma) = \log P(Y | X, \sigma) + \log P(X | \Lambda) + \log P(\Lambda) + \log P(\sigma) \quad (13)$$

$$= -\frac{1}{2} \sum_{t=1}^{T} \left[ (Y(t) - AX(t))^T \sigma \sum_{y0}^{-1} (Y(t) - AX(t)) + X(t)^T W^{-1T} \bigwedge W^{-1} X(t) \right] -$$

$$\sum_{i=1}^{N} \gamma_{pi} \lambda_{pi}^{-1} \lambda_i + \sum_{i=1}^{N} \left( \gamma_{pi} + \frac{T}{2} - 1 \right) \log \lambda_i +$$

$$\left( \frac{MT}{2} - 1 \right) \log \sigma + \text{const.}$$

Since the posterior distribution cannot be analytically obtained, a variational Bayesian method is used. In the variational Bayesian method, instead of directly calculating the posterior distribution, a trial posterior distribution $Q(X,\Lambda,\sigma)$ is prepared, and approximation of true posterior distribution $P(X,\Lambda,\sigma|Y)$ is performed. This approximation is performed by maximizing a free energy F(Q) defined by Equations 14 and 15 below.

$$F(Q) = \int dX d\bigwedge d\sigma Q(X, \Lambda, \sigma) \log \frac{P(Y, X, \Lambda, \sigma)}{Q(X, \Lambda, \sigma)}. \quad (14)$$

$$F(Q) = \log P(Y) - KL[Q(X, \Lambda, \sigma) \| P(X, \Lambda, \sigma | Y)]. \quad (15)$$

Equation 15 is obtained by rewriting Equation 14. In Equation 15, KL is a Kullback-Leibler distance. The first term in Equation 15 does not depend on Q, and, thus, the maximizing the free energy is equivalent to the minimizing the Kullback-Leibler distance between the true posterior distribution and the trial posterior distribution in the second term.

In this case, if an factorization assumption is placed between X and $\Lambda,\sigma$ in the trial posterior distribution, the calculation can be easily performed (see Equation 16).

$$Q(X, \Lambda, \sigma) = Q_X(X) Q_\Lambda(\Lambda, \sigma). \quad (16)$$

With this assumption, the free energy can be maximized by alternately repeating an "X maximizing step" of maximizing F(Q) regarding $Q_X$ and a "$\Lambda,\sigma$ maximizing step" of maximizing F(Q) regarding $Q_\Lambda$.

In this case, the free energy is represented by Equation 17 below.

$$F = -\frac{1}{2} \sum_{t=1}^{T} \left[ (Y(t) - AX(t))^T \sigma \sum_{y0}^{-1} (Y(t) - AX(t)) + X(t)^T W^{-1T} \bigwedge W^{-1} X(t) \right] - \quad (17)$$

$$\frac{T}{2} \log \left| AW \bigwedge^{-1} W^T A^T + \sigma^{-1} \sum_{y0} \right| +$$

$$\sum_{i=1}^{N} \gamma_{pi} [\log(\lambda_i / \lambda_{pi}) - \lambda_i / \lambda_{pi} + 1]$$

$$= -\frac{1}{2} \left[ \sigma \left\| \sum_{y0}^{-\frac{1}{2}} (Y - AX) \right\|^2 + \left\| \Lambda^{\frac{1}{2}} W^{-1} X \right\|^2 + f(\Lambda, \sigma) \right].$$

Equation 9 is obtained by simplifying Equation 17. In Equation 17, X, $\Lambda$, and $\sigma$ represent an expected value of the distribution.

Next, an algorithm of the hierarchical Bayesian estimation performed by the sparseness applying part 244 will be described.

The sparseness applying part 244 repeats "X maximizing step" and "$\Lambda,\sigma$ maximizing step" K times (e.g., K=1000) with an initial value $\lambda_{0i} = (10 \cdot \hat{X}_{Ri})^{-2}$ and $\sigma_0 = 1$.

Note that the "X maximizing step" is represented by Equations 18 to 20 below, and the "$\Lambda,\sigma$ maximizing step" is represented by Equation 21 to 24 below.

Lastly, the sparseness applying part 244 performs the "X maximizing step", thereby obtaining a solution $\hat{X}_B$ (see Equation 25).

$$\sum_{k} = \sigma_{k-1}^{-1} \sum_{y0} + AW \bigwedge_{k-1}^{-1} W^T A^T, \quad (18)$$

$$H_k = \text{diag}\left[\bigwedge_{k-1}^{-1} W^T A^T \sum_{k}^{-1} YY^T \sum_{k}^{-1} AW + T\left(I - \bigwedge_{k-1}^{-1} W^T A^T \sum_{k}^{-1} AW\right)\right]. \quad (19)$$

$$I_k = tr\left[\sigma_{k-1}^{-1} \sum_{y0} \sum_{k}^{-1} YY^T \sum_{k}^{-1} + T \bigwedge_{k-1}^{-1} W^T A^T \sum_{k}^{-1} AW\right] \quad (20)$$

$$\gamma_{k,i} = \gamma_{pi} + \frac{T}{2} \quad (21)$$

$$\gamma_{k,i}\lambda_{k,i}^{-1} = \gamma_{pi}\lambda_{pi}^{-1} + \frac{1}{2}H_{k,i,i}\lambda_{k-1,i}^{-1} \quad (22)$$

$$\gamma_{\sigma k} = \frac{1}{2}MT \quad (23)$$

$$\gamma_{\sigma k}\sigma_k^{-1} = \frac{1}{2}I_k\sigma_{k-1}^{-1} \quad (24)$$

$$\hat{X}_B = W \bigwedge_{k-1}^{-1} W^T A^T \sum_{K}^{-1} Y \quad (25)$$

In Equations 21 and 23, T is the number of time sample data sets. In Equation 23, M is the number of channels.

The output unit 25 outputs the optical characteristic-changed region information acquired by the sparseness applying part 244. Typically, the output unit 25 graphically outputs the optical characteristic-changed region information. However, there is no limitation on the output mode of the optical characteristic-changed region information.

The output is a concept that encompasses display on a display screen, projection using a projector, printing in a printer, output of a sound, transmission to an external apparatus, accumulation in a storage medium, and delivery of a processing result to another processing apparatus or another program.

The reference light intensity information storage unit 21, the sensitivity information storage part 241, and the arithmetic expression storage part 242 are preferably a non-volatile storage medium, but may be realized also by a volatile storage medium.

There is no limitation on the procedure in which the reference light intensity information and the like are stored in the reference light intensity information storage unit 21 and the like. For example, the reference light intensity information and the like may be stored in the reference light intensity information storage unit 21 and the like via a storage medium, the reference light intensity information and the like transmitted via a communication line or the like may be stored in the reference light intensity information storage unit 21 and the like, or the reference light intensity information and the like input via an input device may be stored in the reference light intensity information storage unit 21 and the like.

The light intensity information acquiring unit 22, the light intensity change information acquiring unit 23, the estimating unit 24, the correcting part 243, and the sparseness applying part 244 may be realized typically by a CPU, a memory, or the like. Typically, the processing procedure of the light intensity information acquiring unit 22 and the like is realized by software, and the software is stored in a storage medium such as a ROM. Note that the processing procedure may be realized also by hardware (a dedicated circuit).

The output unit 25 may be considered to include or not to include an output device such as a display screen. The output unit 25 may be realized, for example, by driver software for an output device, a combination of driver software for an output device and the output device, or the like.

Next, an operation of the object observing apparatus 2 will be described with reference to the flowchart in FIG. 2.

(Step S201) The light intensity information acquiring unit 22 acquires light intensity information, which is information regarding a light intensity of light received by each light-receiving probe, in a case where light with a certain light intensity is transmitted from each light-transmitting probe forming each probe set to an object.

(Step S202) The light intensity change information acquiring unit 23 reads reference light intensity information from the reference light intensity information storage unit 21.

(Step S203) The light intensity change information acquiring unit 23 calculates light intensity change information from the light intensity information acquired in step S201 and the reference light intensity information read in step S202.

(Step S204) The estimating unit 24 reads an arithmetic expression from the arithmetic expression storage part 242.

(Step S205) The estimating unit 24 reads sensitivity information from the sensitivity information storage part 241. For example, the sensitivity information is calculated in advance by the estimating unit 24 and is stored in the sensitivity information storage part 241.

(Step S206) The estimating unit 24 estimates optical characteristic-changed region information using the light intensity change information. This processing is referred to as estimation processing. Hereinafter, the estimation processing will be described with reference to the flowchart in FIG. 3.

(Step S207) The output unit 25 outputs the optical characteristic-changed region information acquired by the sparseness applying part 244. The procedure returns to step S201.

Figure 2:
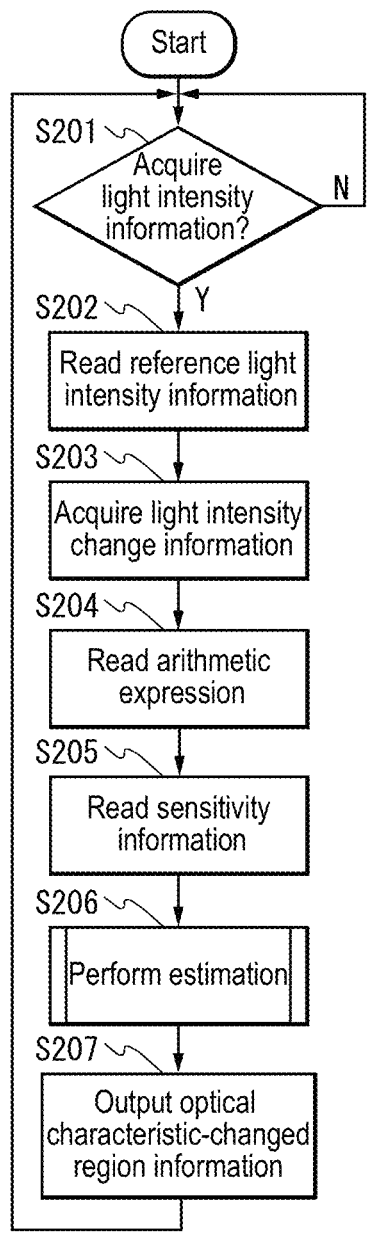
FIG. 2 is a flowchart illustrating an operation of an object observing apparatus in this embodiment.

Note that the process is terminated by powering off or an interruption at completion of the process in the flowchart in FIG. 2.

Figure 3:
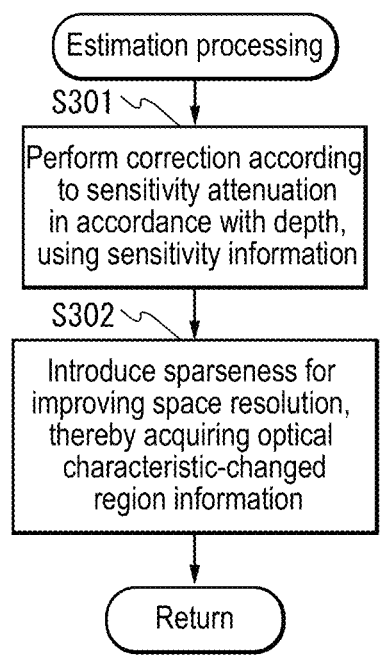
FIG. 3 is a flowchart illustrating an operation of estimation processing in this embodiment.

Next, the estimation processing in step S206 will be described with reference to the flowchart in FIG. 3.

(Step S301) The correcting part 243 performs correction according to sensitivity attenuation in accordance with the depth, using the sensitivity information in the sensitivity information storage part 241. That is to say, the correcting part 243 substitutes the sensitivity information for the first arithmetic expression (arithmetic expression for performing estimation processing of optical characteristic-changed region information with correction according to the sensitivity), thereby acquiring first optical characteristic-changed region information.

(Step S302) The sparseness applying part 244 introduces sparseness for improving the space resolution, using the first optical characteristic-changed region information acquired in step S301 as input, thereby acquiring final optical characteristic-changed region information.

Figure 4:
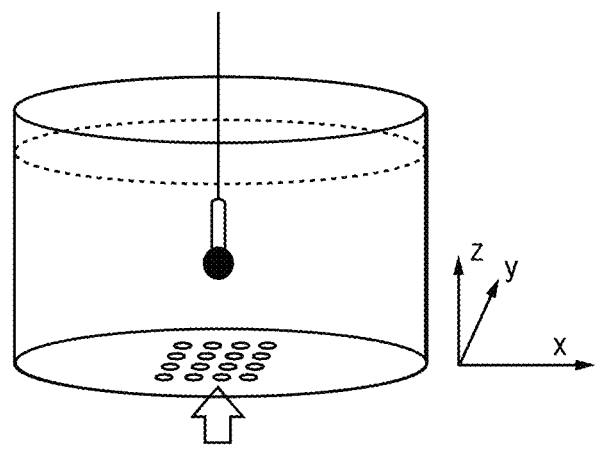
FIG. 4 is a schematic diagram of an experiment using the object observing system in this embodiment.

Hereinafter, experiments using the object observing system in this embodiment will be described. FIG. 4 is a schematic diagram of an experiment (phantom experiment) using the object observing system. In this phantom experiment, near-infrared light was transmitted from one direction to an object, and backscattered light was received from the same direction as the one direction. Furthermore, in this experiment, a tank phantom was used to obtain data for examining the estimation method realized by the object observing apparatus 2.

Figure 5:
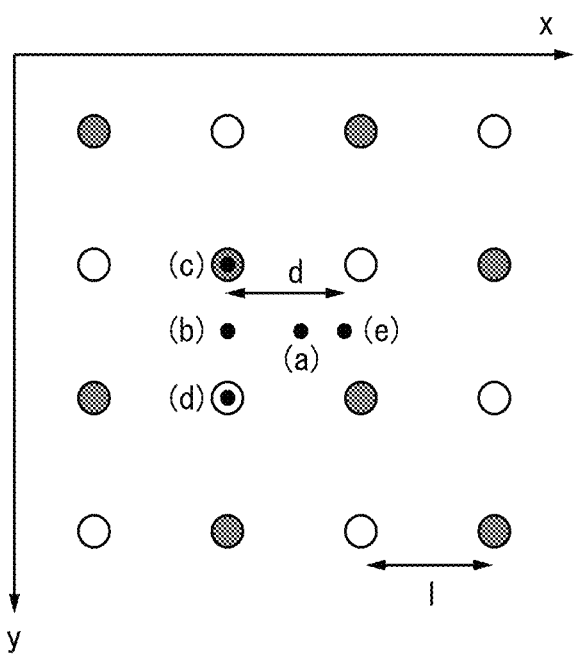
FIG. 5 is a diagram illustrating positions of light-transmitting probes and light-receiving probes in a phantom experiment in this embodiment.

In this experiment, near-infrared light was transmitted and received by the light-transmitting probes 11 and the light-receiving probes 12 at a bottom face of the phantom tank. FIG. 5 is a diagram illustrating positions of the light-transmitting probes 11 and the light-receiving probes 12 and positions of light absorbing members. In FIG. 5, gray circles represent the light-transmitting probes 11, and white circles represent the light-receiving probes 12. The probes are arranged at intervals of 1. Hereinafter, the positions at which the light absorbing members were placed will be described. In FIG. 5, (a) is the center (coordinate values (0, 0)), (b) is a middle point (−½, 0), (c) is the position of one source (the light-transmitting probe 11) (−½, −½), (d) is the position of one detector (the light-receiving probe 12) (−½, +½), and (e) is the position of a second light absorbing member (−½+d, 0). In the diagram, the horizontal distance between two light absorbing members is d.

In this experiment, the tank was filled with 1.4% Intralipid and ink mixture liquid so as to realize the optical characteristics similar to those of the grey matter of the cerebral cortex. The estimated values of the optical parameters based on measurement using a spectrophotometer and a near-infrared imaging device were as follows: absorption coefficient $\mu_a$=0.019 mm$^{-1}$; and reduced scattering coefficient $\mu'_s$=1.1 mm$^{-1}$.

A light absorbance change was measured using a near-infrared imaging device (FOIRE-3000, Shimadzu Corporation). In this experiment, only a wavelength of 805 nm was used for measurement. Near-infrared light was irradiated in a time-divided manner from the light-transmitting probes 11 arranged on a square grid on the bottom face "z=0" of the tank, and was received by the light-receiving probes 12. The sampling rate was set to 130 ms, and the measurement was performed for 20 seconds/each. The experiment was performed with three types of probe intervals, namely 13 mm, 18.4 mm (=13 mm×√2), and 26 mm (=13 mm×2).

Furthermore, in the experiment, one or two spherical light absorbing members each having a diameter of 5 mm were arranged in the liquid. In the experiment with one light absorbing member, measurement was performed for four points, namely (a) the center, (b) the middle point between the light-transmitting probe 11 and the light-receiving probe 12, (c) the position directly below the light-transmitting probe 11, and (d) the position directly below the light-receiving probe 12 (see FIG. 5). In the experiment with two light absorbing members, measurement was performed while arranging the light absorbing members at (b) and (e), which was apart from (b) by d.

Experiment 1

Figure 6:
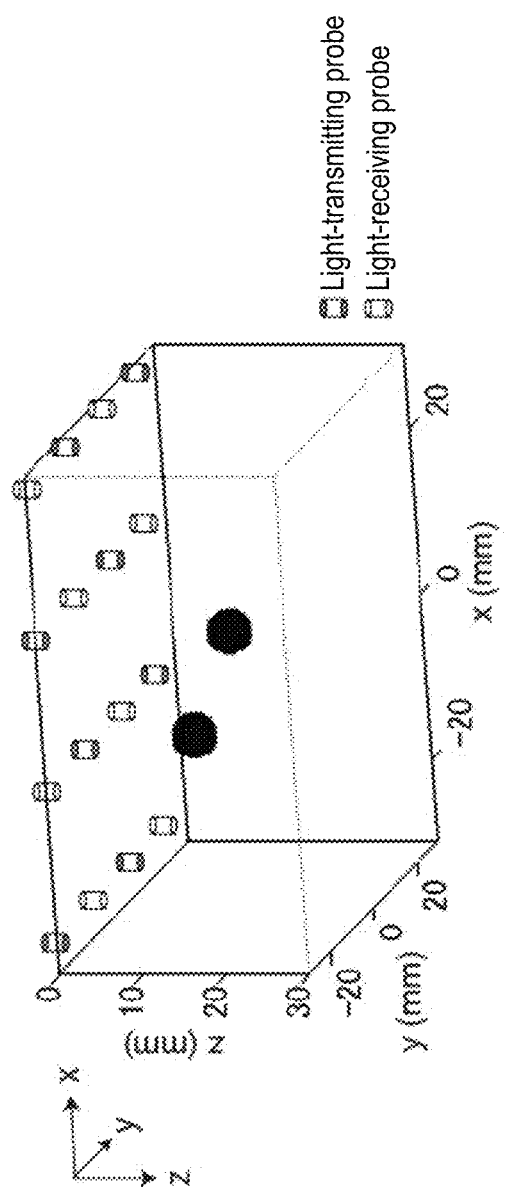
FIG. 6 is a diagram illustrating an environment of Experiment 1 in this embodiment.

Hereinafter, a three-dimensional reconstruction method using observation data in an actual phantom experiment will be described. In Experiment 1, the data measurement condition was such that the light-transmitting probes 11 and the light-receiving probes 12 arranged on the plane with z=0 were used for measurement (see FIG. 6). The probe interval in Experiment 1 was set to 18.4 mm. Two spherical light absorbing members each having a diameter of 5 mm were arranged to cause light absorbance changes. The center coordinates (x, y, z) of the two light absorbing members were respectively (−9.2 mm, 0 mm, 10 mm) and (3.3 mm, 0 mm, 15 mm), that is, they were apart from each other by 12.5 mm in the horizontal direction and 5 mm in the vertical direction, which were distances shorter than the probe interval. Note that the coordinate system in FIG. 6 is obtained by turning that in FIG. 4 upside down. The reason for this is to make the coordinate system correspond to that in measurement of the brain functions where the probe plane is typically positioned on the upper side.

Figure 7:
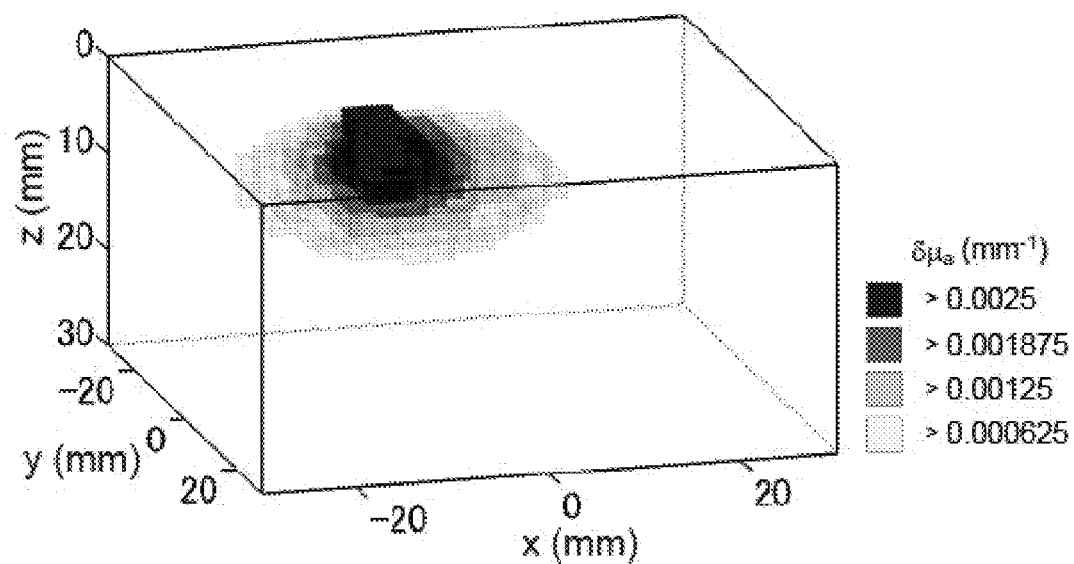
FIG. 7 is a diagram showing an estimation result using a Tikhonov regularization method in a case where a regularization term is not normalized with the sensitivity in this embodiment.

FIG. 7 is an estimation result using the Tikhonov regularization method in a case where D was taken as an identity matrix. Note that taking D as an identity matrix means not performing correction of the regularization term according to the sensitivity attenuation. As shown in FIG. 7, the position obtained as a solution was closer to the probe plane than the actual position was because the sensitivity was exponentially attenuated in accordance with the depth. Furthermore, as shown in FIG. 7, two light absorbance changes were not separated from each other.

Figure 8:
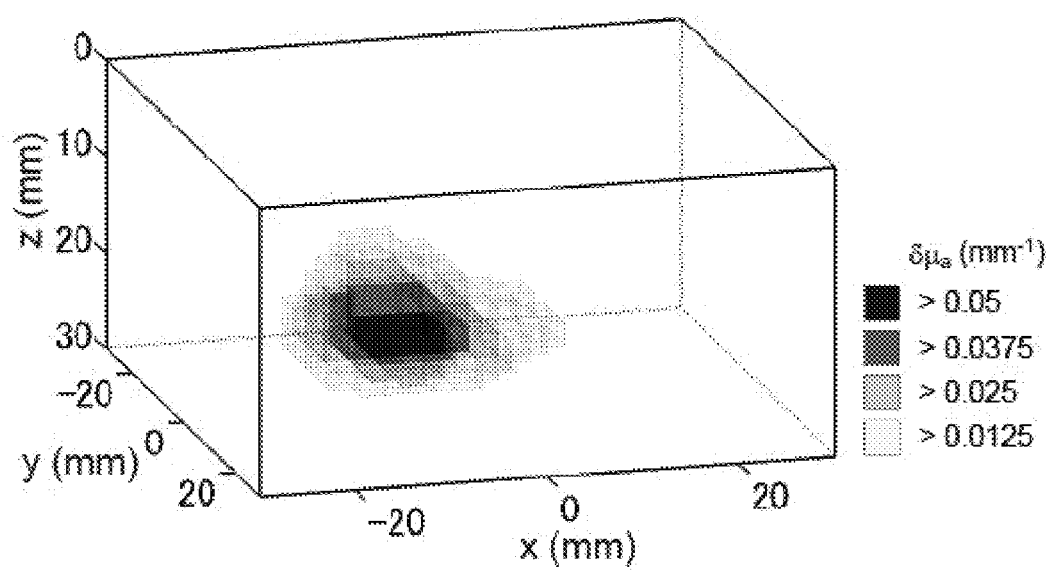
FIG. 8 is a diagram showing an estimation result in a case where the regularization term is normalized with the sensitivity in this embodiment.

FIG. 8 is an estimation result in a case where the regularization term is normalized with the sensitivity. FIG. 8 shows a result that conversely seems to be biased in the depth direction, which is meaningful. Shallow and weak activities and deep and strong activities provide similar observed values, and the Tikhonov regularization method cannot localize the solution, and, thus, the estimation result is obtained as an overlap (coexistence) state thereof. It seems that, since deep and strong activities are more outstanding, the estimation result seems to be biased in the depth direction.

Figure 9:
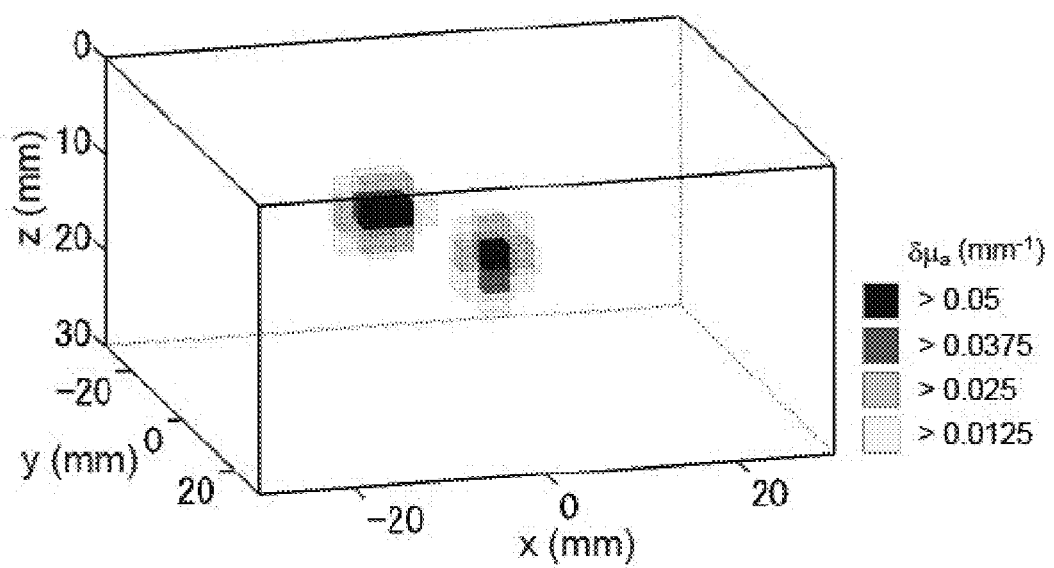
FIG. 9 is a diagram showing an estimation result in a case where application is made to a hierarchical Bayesian method in this embodiment.

FIG. 9 is obtained by performing estimation, using the result in FIG. 8 as an initial value "$\lambda_{0i}=(10 \cdot X^{\hat{}}_{Ri})^{-2}$" in the hierarchical Bayesian method. That is to say, FIG. 9 shows an estimation result (acquisition result of the optical characteristic-changed region information) by the object observing apparatus 2. Since the estimation result of the Tikhonov regularization method is excessively smoothed, a value obtained by multiplying ten by the estimated value was used as an initial value (the same is applied to other experiments below). The sparseness applying part 244 of the estimating unit 24 uses the hierarchical Bayesian algorithm to select an appropriate state from among various solution overlap states obtained in FIG. 8. Accordingly, the sparseness applying part 244 obtains a more accurate estimation result. In Experiment 1, each position of the two light absorbing members was identified, and a difference from the actual positions was one voxel or smaller.

Experiment 2

In Experiment 2, it was examined whether or not the depth was correctly estimated by placing the light absorbing member at the center position ((a) in FIG. 5) and changing the depth by 2.5 mm each time. The measurement was performed with three types of probe intervals, namely 26 mm, 18.4 mm, and 13 mm.

Figure 10:
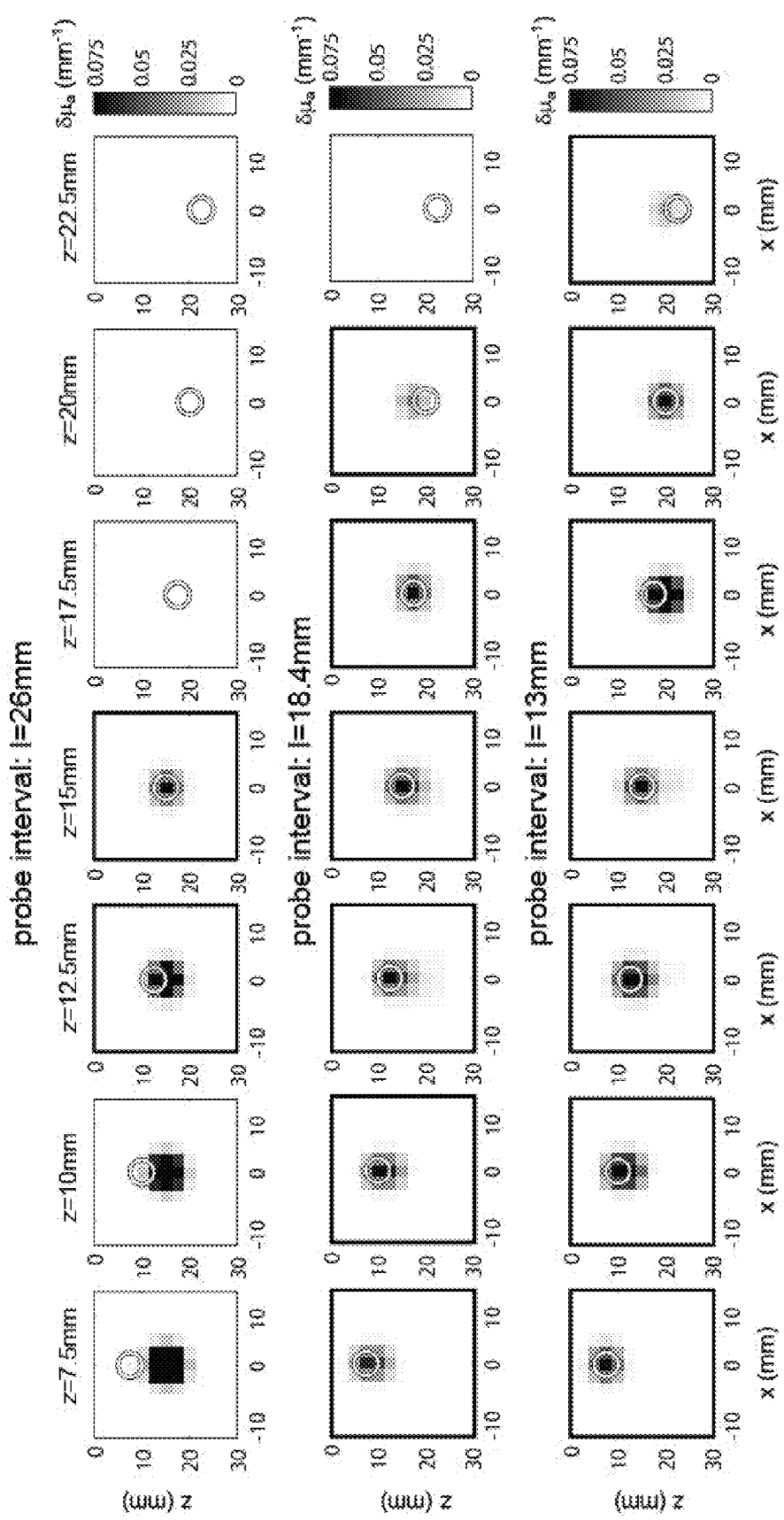
FIG. 10 shows diagrams of a result of estimation performed while changing the probe interval and the depth position of a light absorbing member in this embodiment.
Figure 11:
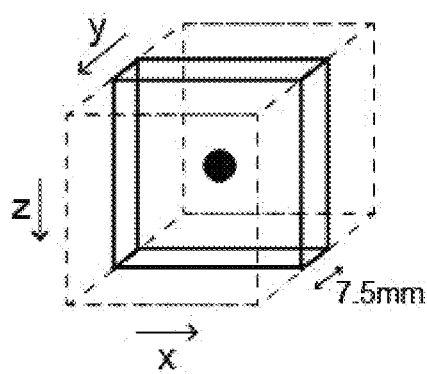
FIG. 11 is a diagram illustrating expressing a three-dimensional estimation diagram in two dimensions in this embodiment.

FIG. 10 shows a result of estimation performed by the object observing apparatus 2 while changing the probe interval and the depth position of the light absorbing member (exemplary output of the optical characteristic-changed region information by the output unit 25). In order to express a three-dimensional estimation diagram in two dimensions, the estimation result is shown such that only the maximum values of three voxels in the vicinity of the center containing the light absorbing member in the y direction are projected on the respective x-z planes as shown in FIG. 11. In FIG. 10, estimation results are shown with a probe interval l=26 mm, 18.4 mm, and 13 mm sequentially from above, and with a true depth z at the center of the light absorbing member=7.5 mm, 10 mm, 12.5 mm, 15 mm, 17.5 mm, 20 mm, and 22.5 mm sequentially from the left. In FIG. 10, white circles represent the true position of the light absorbing member. If a positional error of the estimation result on each of the x, y, and z axes was one voxel or smaller (2.5 mm or less) and an estimated maximum value was $0.025 \text{ mm}^{-1}$ or more, it is considered that the estimation was performed, and the corresponding graph is enclosed by a heavy line.

Figure 12:
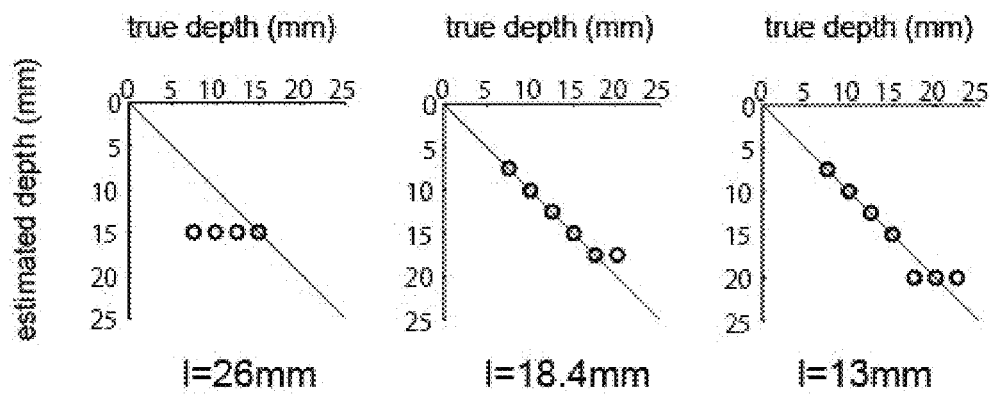
FIG. 12 shows graphs of a result of Experiment 2 in this embodiment.

In the uppermost line (result with a probe interval of 26 mm) in FIG. 10, the estimation results indicate the same depth in the case where the true depth z of the light absorbing member was 7.5 mm to 15 mm (see the left graph in FIG. 12). This result indicates that it was not substantially possible to estimate the depth. Furthermore, it was not possible to perform the estimation in the case where z was 17.5 mm or more.

In the middle line (result with a probe interval of 18.4 mm) in FIG. 10, in the case where the true depth z of the light absorbing member was 7.5 mm to 20 mm, the estimation was possible and the true depth and the estimated depth matched each other within an error of one voxel or smaller (see the middle graph in FIG. 12).

In the lowermost line (result with a probe interval of 13 mm) in FIG. 10, in the case where the true depth z of the light absorbing member was 7.5 mm to 22.5 mm, the estimation was possible and the true depth and the estimated depth matched each other within an error of one voxel or smaller (see the right graph in FIG. 12). It was seen that the depth of a region with a light absorbance change can be accurately estimated in this manner according to high density measurement with a probe interval of 18.4 mm or 13 mm, for example.

Next, in order to investigate the degree of the estimation result depending on the probe relative position, the limit depth was checked at which a positional error of the estimation result on each of the x, y, and z axes was one voxel or smaller and an estimated maximum value was $0.025 \text{ mm}^{-1}$ or more, by placing the light absorbing member at one of the four locations, namely (a) the center, (b) the middle point, (c) the position of the light-transmitting probe 11, and (d) the position of the light-receiving probe 12 in FIG. 5, and increasing the depth by 2.5 mm each time. FIG. 13 shows the result. Note that, in the case where the probe interval was 26 mm, estimation of the depth was not possible, and, thus, correct values of only x and y were regarded as sufficient. It is seen that, with high density measurement, the estimation can be accurately performed without so much depending on the position of the light absorbing member. Furthermore, it is seen that the depth that can be estimated increases as the probe interval is shorter.

Experiment 3

In Experiment 3, in order to check the space resolution according to the hierarchical Bayesian method used by the object observing apparatus 2, the number of light absorbing members was increased to two, and the experiment was performed. The x, y coordinates of the light absorbing members were respectively set to (−½, 0) and (−½+d, 0) ((b) and (e) in FIG. 5), and the horizontal distance between the centers was indicated as d.

Experiment 3 was carried out only with two types of probe intervals, namely 18.4 mm and 13 mm. Since Experiment 2 shows that three-dimensional reconstruction is not possible in the case where the probe interval is 26 mm, this probe interval was not applied to Experiments 3 and 4.

Figure 14:
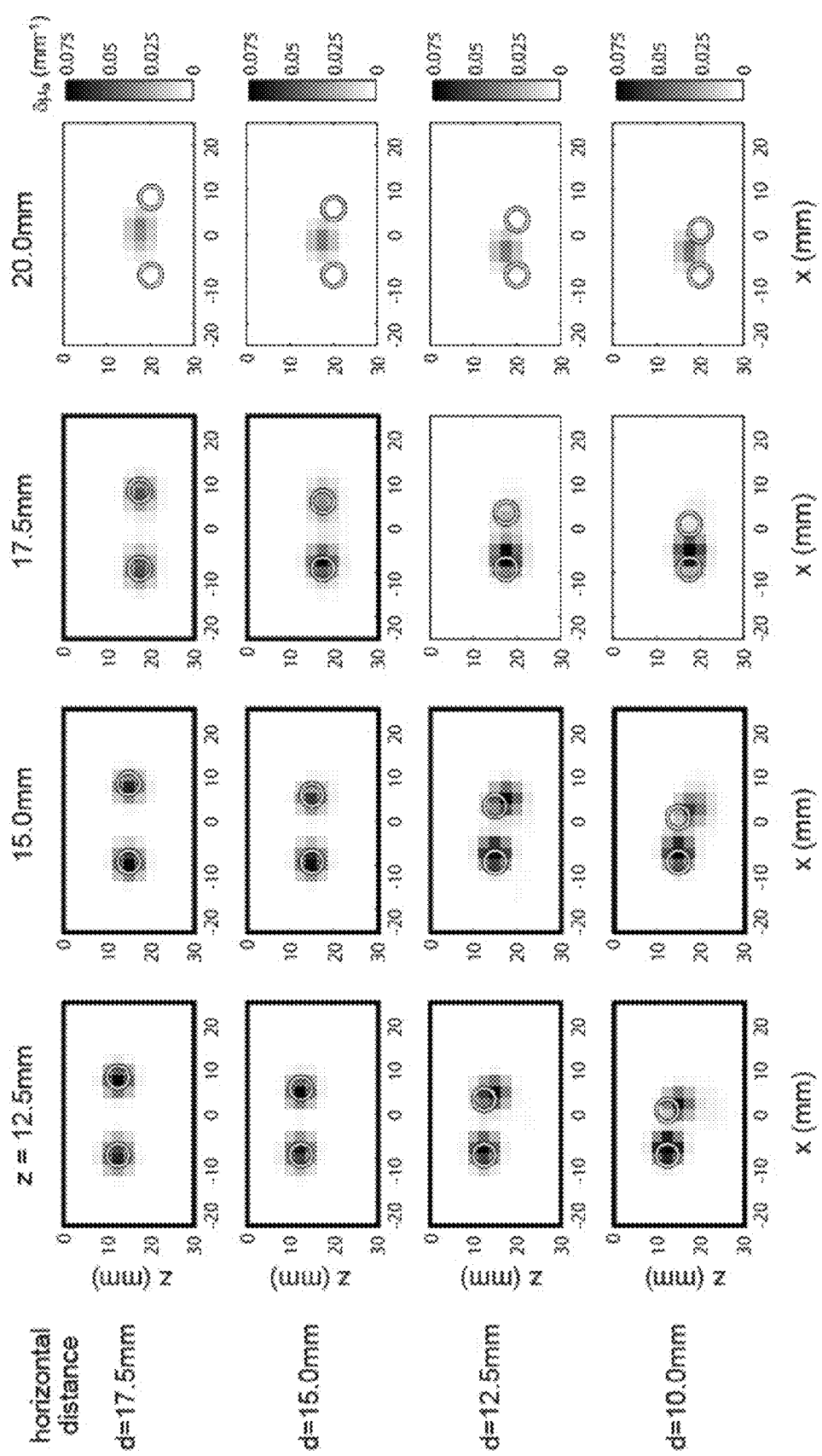
FIG. 14 shows diagrams of a result of Experiment 3 in this embodiment.

FIG. 14 shows an output result (estimation result) of the object observing apparatus 2 at a probe interval of 18.4 mm. This experiment was performed while changing the horizontal distance d and the depth z of the two light absorbing members by 2.5 mm each time. In order to express a three-dimensional estimation diagram in two dimensions as in FIG. 10, the estimation result is shown such that only the maximum values of three voxels in the vicinity of the center containing the light absorbing members in the y direction are projected on the respective x-z planes as shown in FIG. 11. In FIG. 14, estimation results are shown with a horizontal distance d=17.5 mm, 15 mm, 12.5 mm, and 10 mm sequentially from above, and with a true depth z at the center of the light absorbing members=12.5 mm, 15 mm, 17.5 mm, and 20 mm sequentially from the left.

If the two light absorbing members were apart from each other by a distance similar to the probe interval as in the case of "d=17.5 mm, z=17.5 mm" shown in FIG. 14, the positions of the two light absorbing members were accurately estimated up to a depth z=17.5 mm.

Furthermore, the estimation was possible also in a case where the distance between the two light absorbing members was shorter than the probe interval. In particular, in the case where the probe interval was 18.4 mm, it was possible to identify the two light absorbing members located such that the distance d between their centers was 10 mm (distance between the outside edges of 5-mm spheres was 5 mm), that is, such that they were apart from each other by a distance approximately half the probe interval (see the diagram with "d=10 mm, z=15 mm" in FIG. 14).

FIG. 15 is a table showing the limit depths at which, in both of the two light absorbing members, a positional error of the estimation result on each of the x, y, and z axes was one voxel or smaller and an estimated absorption coefficient change was $0.025 \text{ mm}^{-1}$ or more, obtained through the experiment setting the probe interval to two types, namely 18.4 mm and 13 mm and the horizontal distance d between the two light absorbing members to 15 mm, 12.5 mm, 10 mm, and increasing the depth z of the light absorbing members by 2.5 mm each time.

Experiment 4

In order to see whether or not three-dimensional estimation including the depth is possible even under complex conditions, Experiment 4 was carried out. Experiment 4 was carried out with two light absorbing members located at depths different from each other by 5 mm. As in Experiment 3, the x, y coordinates of the light absorbing members were respectively set to (−½, 0) and (−½+d, 0) ((b) and (e) in FIG. 5), and the horizontal distance between the centers was indicated as d. Furthermore, the light absorbing member at (b) was placed at a position shallower than the light absorbing member at (e) by 5 mm. Experiment 4 was carried out only with two types of probe intervals at which the depth estimation was possible, namely 18.4 mm and 13 mm.

Figure 16:
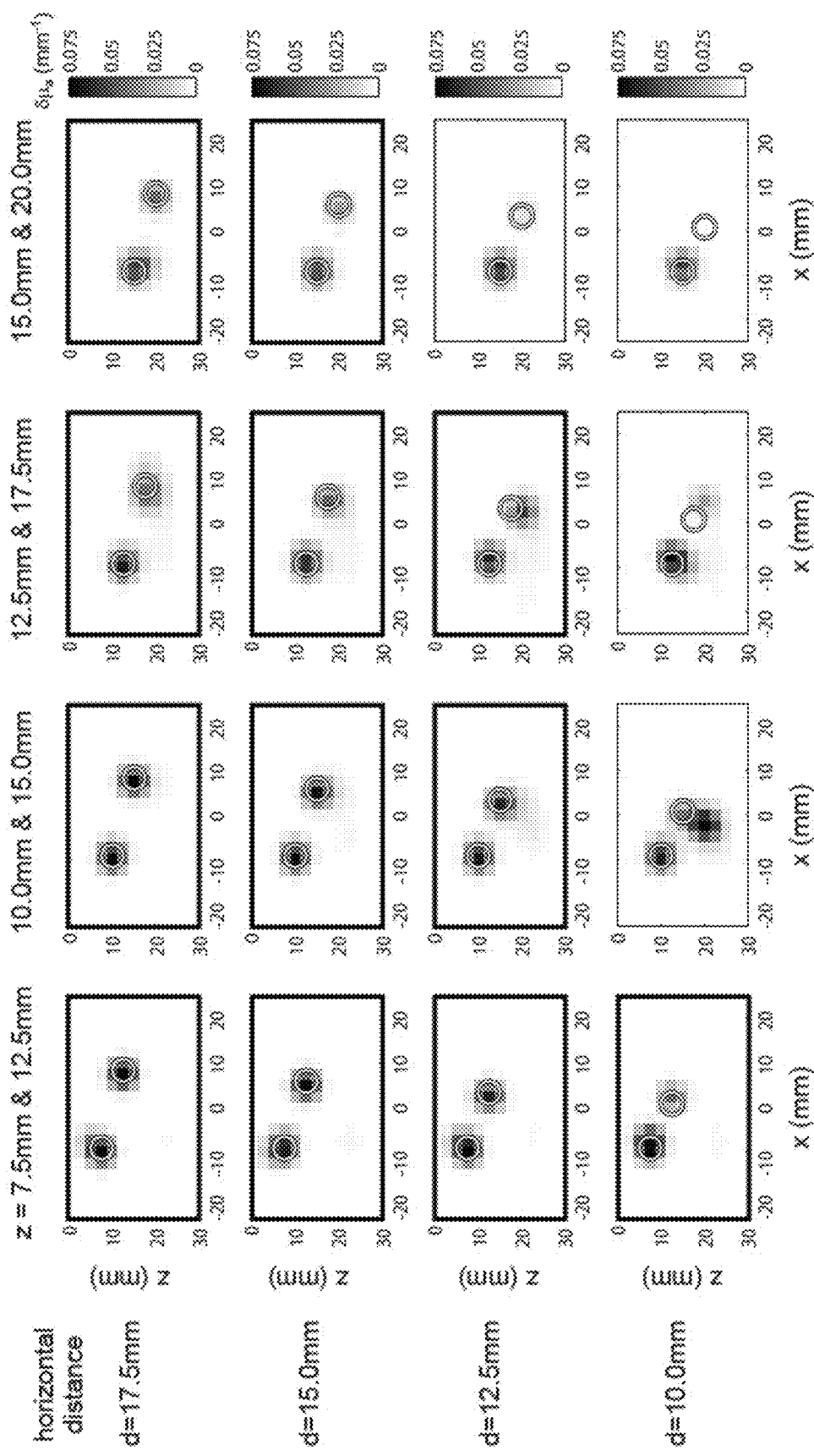
FIG. 16 shows diagrams of a result of Experiment 4 in this embodiment.

FIG. 16 shows an estimation result at a probe interval of 18.4 mm. Experiment 4 was performed while changing the horizontal distance d and the depth z of the two light absorbing members by 2.5 mm each time. In order to express a three-dimensional estimation diagram in two dimensions as in FIG. 10, the estimation result is shown such that only the maximum values of three voxels in the vicinity of the center containing the light absorbing members in the y direction are projected on the respective x-z planes.

As seen from FIG. 16, if the two light absorbing members were apart from each other by a distance similar to the probe interval as in the case of "d=17.5 mm, z=15 & 20 mm" shown in FIG. 16, the position of one light absorbing member at an estimation limit depth z=20 mm was accurately estimated without being interrupted by the other light absorbing member located at a shallower position.

Furthermore, the estimation was possible also in a case where the distance between the two light absorbing members was shorter than the probe interval. It seems that, even if there are multiple light absorbing members located at different depths, high space resolution can be obtained according to the estimation method used by the object observing apparatus 2.

FIG. 17 is a table showing the limit depths at which, in both of the two light absorbing members, a positional error of the estimation result on each of the x, y, and z axes was one voxel or smaller and an estimated absorption coefficient change was 0.025 $mm^{-1}$ or more, obtained through the experiment setting the probe interval to two types, namely 18.4 mm and 13 mm and the horizontal distance d between the two light absorbing members to 15 mm, 12.5 mm, 10 mm, and increasing the depth z of the light absorbing members by 2.5 mm each time.

As described above, this embodiment can accurately estimate, as three-dimensional information, a local optical characteristic-changed region inside an object. More specifically, a local optical characteristic-changed region inside an object can be accurately estimated as three-dimensional information by the high-accuracy three-dimensional reconstruction algorithm including the depth direction, used by this object observing system. Note that the reconstruction algorithm used by the object observing system includes two steps below. Firstly, estimation is performed using the Tikhonov regularization method in which the regularization term is normalized with the sensitivity, so that spatially extended solution candidates are obtained. Secondly, hierarchical Bayesian estimation is performed using the estimation result as an initial value, so that solution candidates are narrowed down to a more appropriate solution.

According to the phantom experiments in this embodiment, in the case where the probe interval was 26 mm, it was not possible for the reconstruction algorithm to operate well due to a lack of observation information, whereas, in the case where the probe interval was 18.4 mm and 13 mm, it was possible to accurately estimate the depth and to identify the two light absorbing members apart from each other by a distance shorter than the probe interval. In particular, in the case where the probe interval was 18.4 mm, it was possible to identify the two light absorbing members located such that the distance between their centers was 10 mm, that is, such that they were apart from each other by a distance approximately half the probe interval.

Furthermore, according to this embodiment, the object observing apparatus 2 introduces sparseness using the hierarchical Bayesian method. However, in this embodiment, it is also possible to introduce sparseness, using an L1 norm. For example, if the second power of the regularization term in Equation 2 is changed to the first power, normalization with the sensitivity and introduction of the sparseness can be simultaneously performed.

Note that estimation using L1 regularization was also actually performed. Also with L1 regularization, the solution becomes sparse, and, thus, a smoothing filter W was introduced in this experiment under the same conditions as those in the case of using the hierarchical Bayesian method. As a result of application to the experimental data, it was found that, if an appropriate regularization parameter k is selected, the estimation can be performed at approximately the same level of precision as the hierarchical Bayesian method. Note that it was seen from this experiment that the correction with the sensitivity and the application of the sparseness can be simultaneously performed. That is to say, the estimating unit, in which sensitivity information, which is information indicating a relationship between an optical characteristic change and a light intensity change, is stored, may perform correction according to sensitivity attenuation in accordance with a depth, using the sensitivity information, and introduce sparseness for improving a space resolution, thereby acquiring optical characteristic-changed region information, wherein the correction with the sensitivity and the application of the sparseness may be simultaneously performed or may be sequentially performed.

Furthermore, the processing in this embodiment may be realized using software. The software may be distributed by software download or the like. Furthermore, the software may be distributed in a form where the software is stored in a storage medium such as a CD-ROM. Note that the same is applied to other embodiments described in this specification. The software that realizes the object observing apparatus 2 in this embodiment may be the following sort of program. Specifically, this program is a program using a storage medium in which reference light intensity information, which is information regarding a light intensity at each light-receiving probe, and is information used as a reference, is stored, the program causing a computer to function as: a light intensity information acquiring unit that, using a near-infrared measurement apparatus having at least one probe set consisting of a pair of a light-transmitting probe for transmitting light to an object that is to be observed and a light-receiving probe for receiving light, acquires light intensity information, which is information regarding a light intensity of light received by each light-receiving probe, in a case where light with a certain light intensity is transmitted from each light-transmitting probe forming each probe set to the object; a light intensity change information acquiring unit that acquires, for each probe set, light intensity change information, which is information regarding a light intensity change, from the reference light intensity information in the storage medium and the light intensity information acquired by the light intensity information acquiring unit; an estimating unit that acquires optical characteristic-changed region information, which is three-dimensional information regarding a position with a light absorbance change inside the object, using the light intensity change information for each probe set; and an output unit that outputs the optical characteristic-changed region information acquired by the estimating unit; wherein the estimating unit includes: a correcting part that performs correction according to sensitivity attenuation in accordance with a depth, using sensitivity information, which is information indicating a relationship between an optical characteristic change and a light intensity change; and a sparseness applying part that introduces sparseness for improving a space resolution, thereby acquiring the optical characteristic-changed region information.

Furthermore, in this program, it is preferable that the computer is caused to function such that the estimating unit further includes an arithmetic expression storage part, in which a first arithmetic expression, which is an arithmetic expression used for acquiring the optical characteristic-changed region information, is an arithmetic expression for calculating a solution of an inverse problem, and is a cost function for performing correction according to the sensitivity information, can be stored, the correcting part substitutes the sensitivity information for the first arithmetic expression, thereby acquiring first optical characteristic-changed region information, the sparseness applying part acquires final optical characteristic-changed region information using the sparseness for improving the space resolution, using the first optical characteristic-changed region information, and the output unit outputs the optical characteristic-changed region information acquired by the sparseness applying part.

Furthermore, in this program, it is preferable that the computer is caused to function such that, in the arithmetic expression storage part, a second arithmetic expression for performing hierarchical Bayesian estimation on an initial value is also stored, and the sparseness applying part substitutes the first optical characteristic-changed region information as an initial value for the second arithmetic expression, and executes the second arithmetic expression to perform hierarchical Bayesian estimation, thereby acquiring final optical characteristic-changed region information.

Furthermore, in this program, it is preferable that the computer is caused to function for observing a brain function of a living body, wherein the object that is to be observed is the brain of the living body, and the reference light intensity information is information regarding a light intensity at each light-receiving probe measured at rest.

Furthermore, in this program, it is preferable that the computer is caused to function for screening of breast cancer, wherein the object that is to be observed is a breast, and the reference light intensity information is information regarding a light intensity at each light-receiving probe from a breast with normal cells.

Furthermore, in this program, it is preferable that the computer is caused to function such that each interval between the light-transmitting and light-receiving probes is not greater than 20 mm.

Figure 18:
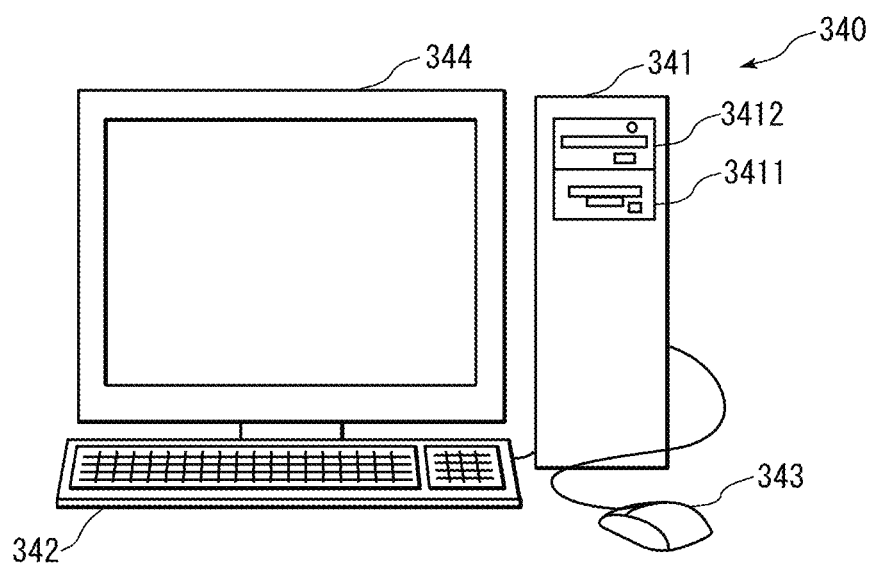
FIG. 18 is a schematic view of a computer system in this embodiment.
Figure 19:
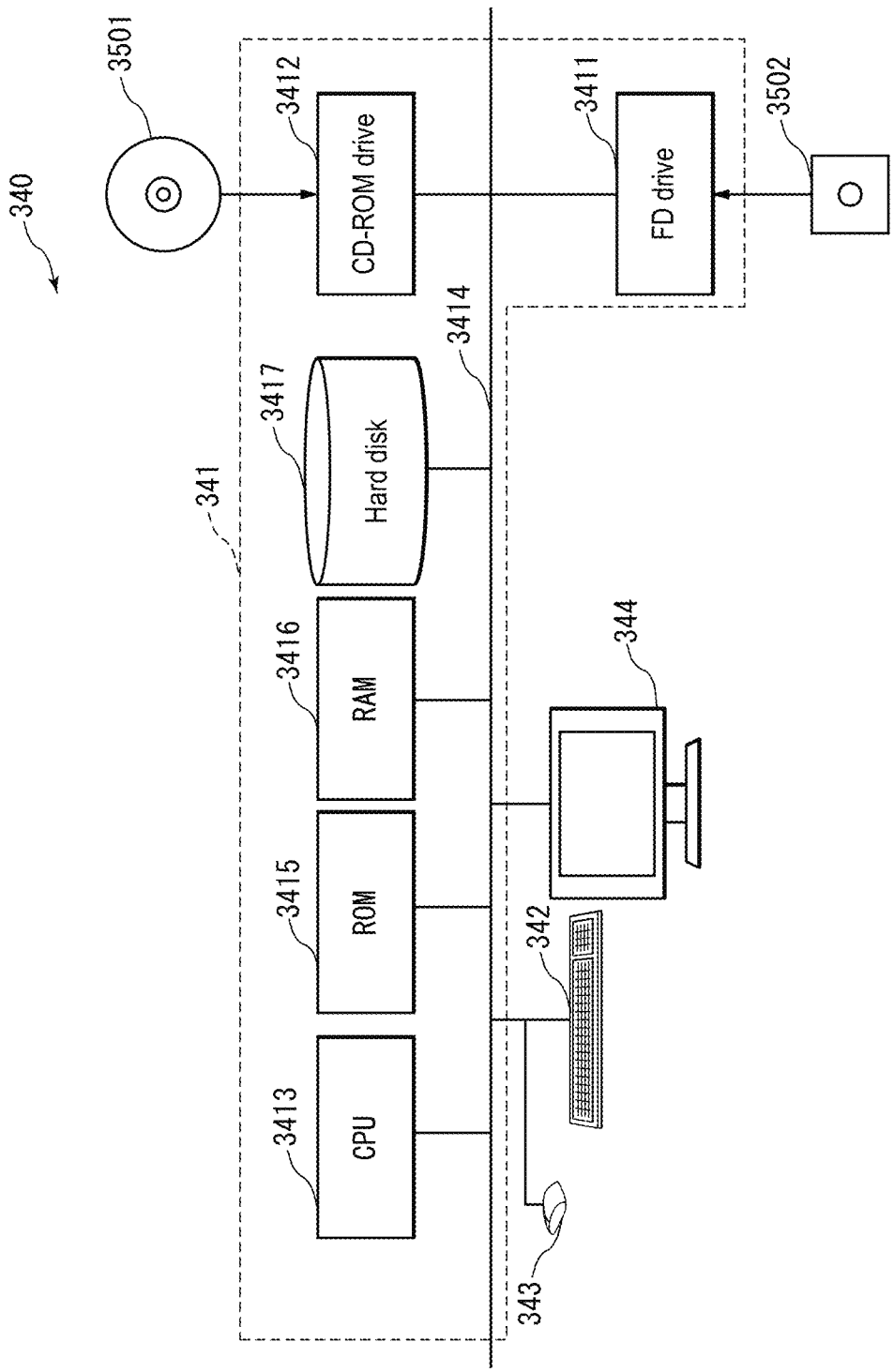
FIG. 19 is a block diagram of the computer system in this embodiment.

FIG. 18 shows the external appearance of a computer that executes the programs described in this specification to realize the object observing apparatus 2 and the like in the foregoing embodiments. The foregoing embodiments may be realized using computer hardware and a computer program executed thereon. FIG. 18 is a schematic view of the computer system. FIG. 19 is a block diagram of the computer system.

In FIG. 18, the computer system 340 includes a computer 341 including an FD drive and a CD-ROM drive, a keyboard 342, a mouse 343, and a monitor 344.

In FIG. 19, the computer 341 includes not only the FD drive 3411 and the CD-ROM drive 3412, but also a CPU 3413, a bus 3414 that is connected to the CD-ROM drive 3412 and the FD drive 3411, a RAM 3416 in which a command of an application program is temporarily stored and a temporary storage area is to be provided, and that is connected to a ROM 3415 in which a program such as a boot up program is to be stored, and a hard disk 3417 in which an application program, a system program, and data are to be stored. Although not shown, the computer 341 may further include a network card that provides connection to a LAN.

The program for causing the computer system 340 to execute the functions of the object observing apparatus and the like in the foregoing embodiments may be stored in a CD-ROM 3501 or an FD 3502, inserted into the CD-ROM drive 3412 or the FD drive 3411, and transmitted to the hard disk 3417. Alternatively, the program may be transmitted via an unshown network to the computer 341 and stored in the hard disk 3417. At the time of execution, the program is loaded into the RAM 3416. The program may be loaded from the CD-ROM 3501 or the FD 3502, or directly from a network.

The program does not necessarily have to include, for example, an operating system (OS) or a third party program to cause the computer 341 to execute the functions of the object observing apparatus and the like in the foregoing embodiments. The program may only include a command portion to call an appropriate function (module) in a controlled mode and obtain the desired results. The manner in which the computer system 340 operates is well known, and, thus, a detailed description thereof has been omitted.

Furthermore, the computer that executes this program may be a single computer, or may be multiple computers. More specifically, centralized processing may be performed, or distributed processing may be performed.

Furthermore, in the foregoing embodiments, each process (each function) may be realized as an integrated process using a single apparatus (system), or may be realized as a distributed process using multiple apparatuses.

It will be appreciated that the present invention is not limited to the embodiments set forth herein, and various modifications are possible within the scope of the present invention.

INDUSTRIAL APPLICABILITY

As described above, the object observing system according to the present invention has an effect that this system can accurately estimate, as three-dimensional information, a local optical characteristic-changed region inside an object, and, thus, this system is useful as a brain function observing system and the like.

The invention claimed is:

1. An object observing apparatus, comprising:
a reference light intensity information storage unit in which reference light intensity information, which is information regarding a light intensity at each light-receiving probe, and is information used as a reference, is stored;
a light intensity information acquiring unit that, using a near-infrared measurement apparatus having at least one probe set consisting of a pair of a light-transmitting probe for transmitting light to an object that is to be observed and a light-receiving probe for receiving light, acquires light intensity information, which is information regarding a light intensity of light received by each light-receiving probe, in a case where light with a certain light intensity is transmitted from each light-transmitting probe forming each probe set to the object;
a light intensity change information acquiring unit that acquires, for each probe set, light intensity change information, which is information regarding a light intensity change, from the reference light intensity information in the reference light intensity information storage unit and the light intensity information acquired by the light intensity information acquiring unit;
an estimating unit that acquires optical characteristic-changed region information, which is three-dimensional information regarding a position with a light absorbance change inside the object, using the light intensity change information for each probe set; and an output unit that outputs the optical characteristic-changed region information acquired by the estimating unit;

wherein the estimating unit, in which sensitivity information, which is information indicating a relationship between an optical characteristic change and a light intensity change, is stored, performs correction according to sensitivity attenuation in accordance with a depth, using the sensitivity information, and introduces sparseness for improving a space resolution, thereby acquiring the optical characteristic-changed region information.

2. The object observing apparatus according to claim 1, wherein the estimating unit includes:

a sensitivity information storage part in which sensitivity information, which is information indicating a relationship between an optical characteristic change and a light intensity change, can be stored;

a correcting part that performs correction according to sensitivity attenuation in accordance with a depth, using the sensitivity information; and a sparseness applying part that introduces sparseness for improving the space resolution, thereby acquiring the optical characteristic-changed region information.

3. The object observing apparatus according to claim 2, wherein the estimating unit further includes an arithmetic expression storage part, in which a first arithmetic expression, which is an arithmetic expression used for acquiring the optical characteristic-changed region information, is an arithmetic expression for calculating a solution of an inverse problem, and is a cost function for performing correction according to the sensitivity information, can be stored, the correcting part substitutes the sensitivity information for the first arithmetic expression, thereby acquiring first optical characteristic-changed region information, the sparseness applying part acquires final optical characteristic-changed region information using the sparseness for improving the space resolution, using the first optical characteristic-changed region information, and the output unit outputs the optical characteristic-changed region information acquired by the sparseness applying part.

4. The object observing apparatus according to claim 3, wherein, in the arithmetic expression storage part, a second arithmetic expression for performing hierarchical Bayesian estimation on an initial value is also stored, and the sparseness applying part substitutes the first optical characteristic-changed region information as an initial value for the second arithmetic expression, and executes the second arithmetic expression to perform hierarchical Bayesian estimation, thereby acquiring final optical characteristic-changed region information.

5. The object observing apparatus according to claim 4, wherein each interval between the light-transmitting and light-receiving probes is not greater than 20 mm.

6. The object observing apparatus according to claim 3, wherein each interval between the light-transmitting and light-receiving probes is not greater than 20 mm.

7. The object observing apparatus according to claim 2, wherein each interval between the light-transmitting and light-receiving probes is not greater than 20 mm.

8. The object observing apparatus according to claim 1, for use in observation of a brain function of a living body, wherein the object that is to be observed is the brain of the living body, and the reference light intensity information is information regarding a light intensity at each light-receiving probe measured at rest.

9. The object observing apparatus according to claim 8, wherein each interval between the light-transmitting and light-receiving probes is not greater than 20 mm.

10. The object observing apparatus according to claim 1, for use in screening of breast cancer, wherein the object that is to be observed is a breast, and the reference light intensity information is information regarding a light intensity at each light-receiving probe from a breast with normal cells.

11. The object observing apparatus according to claim 10, wherein each interval between the light-transmitting and light-receiving probes is not greater than 20 mm.

12. The object observing apparatus according to claim 1, wherein each interval between the light-transmitting and light-receiving probes is not greater than 20 mm.

13. An object observing method using a storage medium in which reference light intensity information, which is information regarding a light intensity at each light-receiving probe, and is information used as a reference, is stored, and realized with a light intensity information acquiring unit, a light intensity change information acquiring unit, an estimating unit, and an output unit, the object observing method comprising:

a light intensity information acquiring step of the light intensity information acquiring unit, using a near-infrared measurement apparatus having at least one probe set consisting of a pair of a light-transmitting probe for transmitting light to an object that is to be observed and a light-receiving probe for receiving light, acquiring light intensity information, which is information regarding a light intensity of light received by each light-receiving probe, in a case where light with a certain light intensity is transmitted from each light-transmitting probe forming each probe set to the object;

a light intensity change information acquiring step of the light intensity change information acquiring unit acquiring, for each probe set, light intensity change information, which is information regarding a light intensity change, from the reference light intensity information in the storage medium and the light intensity information acquired in the light intensity information acquiring step;

an estimating step of the estimating unit acquiring optical characteristic-changed region information, which is three-dimensional information regarding a position with a light absorbance change inside the object, using the light intensity change information for each probe set; and an output step of the output unit outputting the optical characteristic-changed region information acquired in the estimating step;

wherein, in the estimating step, correction is performed according to sensitivity attenuation in accordance with a depth, using sensitivity information, which is information indicating a relationship between an optical characteristic change and a light intensity change, and sparseness is introduced for improving a space resolution, so that the optical characteristic-changed region information is acquired.

14. A non-transitory computer readable storage medium in which a program is stored, and in which reference light intensity information, which is information regarding a light intensity at each light-receiving probe, and is information used as a reference, is stored, the program causing the computer to function as:
- a light intensity information acquiring unit that, using a near-infrared measurement apparatus having at least one probe set consisting of a pair of a light-transmitting probe for transmitting light to an object that is to be observed and a light-receiving probe for receiving light, acquires light intensity information, which is information regarding a light intensity of light received by each light-receiving probe, in a case where light with a certain light intensity is transmitted from each light-transmitting probe forming each probe set to the object;
- a light intensity change information acquiring unit that acquires, for each probe set, light intensity change information, which is information regarding a light intensity change, from the reference light intensity information in the storage medium and the light intensity information acquired by the light intensity information acquiring unit;
- an estimating unit that acquires optical characteristic-changed region information, which is three-dimensional information regarding a position with a light absorbance change inside the object, using the light intensity change information for each probe set; and
- an output unit that outputs the optical characteristic-changed region information acquired by the estimating unit;

wherein the estimating unit performs correction according to sensitivity attenuation in accordance with a depth, using sensitivity information, which is information indicating a relationship between an optical characteristic change and a light intensity change, and introduces sparseness for improving a space resolution, thereby acquiring the optical characteristic-changed region information.

* * * * *